United States Patent [19]

Rimbault

[11] Patent Number: 4,885,298

[45] Date of Patent: Dec. 5, 1989

[54] PHARMACEUTICAL PREPARATIONS CONTAINING FLAVANONE OR THIOFLAVANONE DERIVATIVES THE USE THEREOF, NOVEL FLAVANONES AND THIOFLAVANONES, AND PROCESSES FOR THEIR MANUFACTURE

[75] Inventor: Christian G. Rimbault, Grand-Lancy, Switzerland

[73] Assignee: Zyma SA, Nyon, Switzerland

[21] Appl. No.: 229,798

[22] Filed: Aug. 2, 1988

Related U.S. Application Data

[63] Continuation of Ser. No. 4,749, Jan. 8, 1987, abandoned, which is a continuation of Ser. No. 644,005, Aug. 24, 1984, abandoned.

[30] Foreign Application Priority Data

Aug. 31, 1983 [GB] United Kingdom ............... 8323291

[51] Int. Cl.$^4$ ............... A61K 31/35; A61K 31/38; C07D 311/32; C07D 335/06
[52] U.S. Cl. ............... 514/253; 514/397; 514/432; 514/456; 544/376; 548/336; 549/23; 549/403
[58] Field of Search ............... 549/23, 403; 548/336; 544/376; 514/253, 397, 432, 456

[56] References Cited

U.S. PATENT DOCUMENTS

| | | | |
|---|---|---|---|
| 2,727,057 | 12/1955 | Park | 549/23 |
| 3,678,044 | 7/1972 | Adams | 549/23 |
| 3,772,243 | 11/1973 | Adams | 549/23 |
| 4,143,139 | 3/1979 | Bindra | 549/23 |
| 4,162,162 | 7/1979 | Dueber | 549/23 |
| 4,228,177 | 10/1980 | Hoehn | 549/23 |
| 4,235,913 | 11/1980 | Johnson | 549/23 |
| 4,241,069 | 12/1980 | Buckler | 549/23 |
| 4,382,951 | 5/1983 | Grassberger et al. | 549/23 |

FOREIGN PATENT DOCUMENTS 1250388  10/1971  United Kingdom ............... 549/432

OTHER PUBLICATIONS

F. E. Ward et al., J. Med. Chem. 24, 1073 (1981).
L. Reichel et al., Liebigs Ann. Chem 720, 154 (1968).
G. Miklos et al., Acta Pharm. Hung. 40, 233 (1970).
F. Morsingh, Tetrahedron 25 (1969).
T. Szell et al., Chem. Asstr. 73 3618a.
J. Adams, J. Org. Chem. 32 3992 (1967).
B. L. Verma et al., Chem. Abstr 64 14160f.
P. Bennett et al., J. Chem. Soc. Perkin Tr. 1, 1972 1554.
H. Whittmann et al., Monatsh Chem 96 1016 (1965).
L. Reichel et al., Liebigs Ann., Chem. 693,216 (1966).
J. R. Doherty et al., Chem. Ind. (London) (1967) 1641.
T. Szell et al., Can. J. Chem. 46 1571 (1968).
J. R. Doherty et al., Tetrah, Lett (1968) 441.
D. D. Keane et al., J. Org. Chem 35 2286 (1970).
J. J. Beirne et al., Chem. Abstr. 89 14629f.
J. J. Beirne et al., Chem. Abstr. 89, 109020v.
A. Levai et al., Pharmazie 33 378 (1978).

Z. Dinya et al., Chem. Abstr. 91, 131467j.
E. R. David et al., Acta Chim. Acad. Sci Hung 104, 369 (1980).
A. Szollosy et al., Acta Chim. Acad. Sci Hung 112, 343 (1983).
A. Levai et al., Chem. Abstr. 98, 34569f.
G. Toth et al., Org. Magn. Res. 20, 133 (1982).
R. Onoda et al., Chem. Abstr. 85, 5450m.
G. Toth et al., Chem. Abstr. 99, 194937y.
CA 93:95152h (1980), P. Valenti et al.
Shen et al., "The Development of Antiasthmatic Drugs", Part III, ed. D. R. Buckle et al., Butterworth Publishers, Kent, England, 1983, pp. 315–317 and 331–335.
Bull. Chem. Soc. Jap. 52:1735–1737 (1979).
Houben–Weyl, 4th ed., vol. XI/1, pp. 34–53, 205–207.
Helv. Chem. Acta, 54:710–734 (1971).
J. Med. Chem. 24:468–472 (1981).
"Methoden der Organischen Chemie", in Houben-Weyl 4th ed., vol. II/2b, pp. 1449–1529 (1976).
Tetrahedron Letters 32:2603–2605 (1976).

(List continued on next page.)

Primary Examiner—Joseph Paul Brust
Assistant Examiner—Mary Sue Howard
Attorney, Agent, or Firm—Irving M. Fishman

[57] ABSTRACT

The invention relates to pharmaceutical preparations containing compounds of formula I

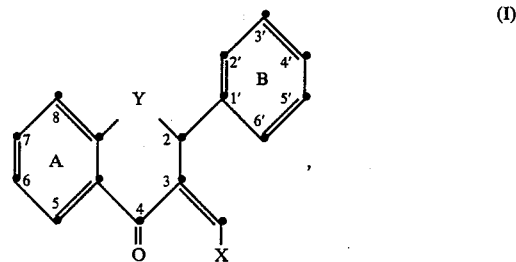

in which X represents unsubstituted or substituted amino or a quaternary ammonium salt; halogen, free, etherified or esterified hydroxy; free, etherified, esterified or oxidized mercapto; free or functionally modified carboxyl, free or functionally modified sulfo; acyl; nitro; an unsubstituted or substituted hydrocarbon radical or an unsubstituted or substituted heterocyclic radical, Y represents oxygen, sulfur, sulfinyl or sulfonyl but must be oxygen, sulfinyl or sulfonyl, if X is 1H-imidazol-1-yl, and rings A and B are each unsubstituted or substituted; or pharmaceutically acceptable salts of such compounds that contain a salt-forming group, and to novel compounds of formula I. The compounds are useful e.g. for the treatment of diseases of the respiratory tract and of liver diseases. They are prepared by methods known per se.

27 Claims, No Drawings

OTHER PUBLICATIONS

Tetrahedron Letters, p. 1015 (1979).
Synthesis, pp. 535–537, 543 (1976).
J. Org. Chem. 40:526–527 (1975).
J.A.C.S. 98:7868–7869 (1976).
J.A.C.S. 93:1027 (1971).
J. Org. Chem. 43:4248–4250 (1978).
J. Org. Chem. 45:4522–4524 (1980).
J. Org. Chem. 27:1615, 1620 (1962).
Meiji, patent abstract Japan, JA-7214573-R, May 1, 1972.
Meiji, patent abstract Japan, JA-7019299-R, Jul. 2, 1970.
Weitsch, Beneficial Therapeutic Effect of Decreased Blood Hyperviscosity in Patients with Vascular Diseases (6/88).

PHARMACEUTICAL PREPARATIONS CONTAINING FLAVANONE OR THIOFLAVANONE DERIVATIVES THE USE THEREOF, NOVEL FLAVANONES AND THIOFLAVANONES, AND PROCESSES FOR THEIR MANUFACTURE

This application is a continuation of Ser. No. 004,749, filed Jan. 8, 1987, now abandoned, which is a continuation of Ser. No. 644,005, filed Aug. 24, 1984, now abandoned.

The invention relates to pharmaceutical preparations containing flavanones, thioflavanones or oxidized derivatives thereof, especially 3-methylideneflavanones and -thio-, -sulfinyl-, or -sulfonylflavanones, the therapeutic use of these compounds, novel compounds of this kind and processes for their manufacture. These compounds have valuable pharmaceutical properties.

The invention relates in particular to pharmaceutical preparations containing compounds of formula I

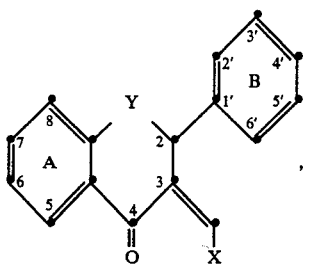

(I)

in which X represents unsubstituted or substituted amino or a quaternary ammonium salt; halogen, free, etherified or esterified hydroxy; free, etherified, esterified or oxidized mercapto; free or functionally modified carboxyl, free or functionally modified sulfo; acyl; nitro; an unsubstituted or substituted hydrocarbon radical or an unsubstituted or substituted heterocyclic radical, Y represents oxygen, sulfur, sulfinyl or sulfonyl but must be oxygen, sulfinyl or sulfonyl, if X is 1H-imidazol-1-yl, and rings A and B are each unsubstituted or substituted; or pharmaceutically acceptable salts of such compounds that contain a salt-forming group.

In case Y is sulfinyl the corresponding sulfoxide compound may exist in its α- or in its β-form.

Within the formula I the group =C-X may be present in the syn(or Z)-form or in the anti(or E)-form.

Unless otherwise noted, "lower" radicals are in particular those having up to 7, especially up to 4, carbon atoms. The term "substituted" in connection with organic groups or radicals always comprises preferably mono- or di- but also polysubstitution. A substituted ring A or B as mentioned before represents a benzene ring substituted e.g. by 1, 2, 3 or 4 substituents.

An unsubstituted or substituted amino group can be a primary, secondary or tertiary amino group. In the two last-mentioned amino groups, the nitrogen atom can carry as substituents unsubstituted or substituted aliphatic, cycloaliphatic, cycloaliphatic-aliphatic, aromatic, araliphatic, heterocyclic or heterocyclic-aliphatic hydrocarbon radicals, or acyl. Two substituents taken together can however also be an unsubstituted or substituted bivalent aliphatic hydrocarbon radical, for example lower alkylene, lower alkenylene or lower alkadienylene, in all of which the carbon atoms of the chain are optionally replaced by 1 or 2, preferably 1, heteroatoms selected from the group comprising e.g. oxygen, sulfur or unsubstituted or substituted nitrogen.

Secondary amino groups are in particular: lower-alkylamino, such as methylamino, ethylamino, n-propylamino, iso-propylamino or di-n-butylamino; cycloalkylamino, e.g. cyclohexylamino; phenyl-lower-alkylamino, e.g. benzylamino; phenylamino; heterocyclylamino, e.g. 2-imidazolylamino; or heterocyclyl-lower-alkylamino, e.g. 2-imidazolylmethylamino, or acylamino.

Tertiary amino groups are in particular: di-lower alkylamino, such as dimethylamino, diethylamino, di-n-propylamino or di-isopropylamino; N-cycloalkyl-N-lower-alkylamino, e.g. N-cyclopentyl-N-methylamino; N-phenyl-N-lower-alkylamino, e.g. N-methyl-N-phenylamino; or N-phenyl-lower-alkyl-N-lower-alkylamino, e.g. N-benzyl-N-methylamino; lower alkyleneamino, aza-, oxa- or thia-lower alkyleneamino, lower alkenyleneamino, lower alkadienyleneamino; or di-acylamino.

Lower alkylamino and di-lower alkylamino groups may optionally be substituted within the lower alkyl portions, preferably by hydroxy and/or free or esterified carboxyl. Advantageously a hydroxy substituent is separated from the amino nitrogen atom by at least 2, preferably 2 or 3, carbon atoms. Such groups are for example: 2-hydroxyethylamino, N-(2-hydroxyethyl)-N-methylamino or di-(2-hydroxyethyl)-amino. Free or esterified carboxyl-substituted lower alkylamino is e.g. (N-carboxymethyl)amino or (N-methoxycarbonylmethyl)amino.

Lower-alkyleneamino having 3 to 8, preferably 5 to 7, ring members is for example: pyrrolidino, 2,5-dimethyl-pyrrolidino, piperidino, 2-methyl-piperidino, 3-ethyl-piperidino, hexahydro-1H-azepino or octahydroazocino. Mentioned as aza-, oxa- or thia-lower alkyleneamino having 6 to 8, preferably 6, ring members, in which an azanitrogen atom is unsubstituted or preferably substituted by for example lower alkyl, hydroxy-($C_2$-$C_7$)-alkyl, phenyl, phenyl-lower-alkyl or pyridyl or acyl, and wherein the hetero atom is separated at least by 2 carbon atoms from the amino-nitrogen atom, are for example piperazino, 4-methylpiperazino, 4-(2-hydroxyethyl)-piperazino, 4-(2",3"-dihydro-2"-phenyl-4"H-1-benzopyran-4-on-3"-ylidene-methyl)-piperazino or 4-acetylpiperazino, further e.g. morpholino and thiomorpholino.

Lower alkenyleneamino has preferably 5 to 7 ring members and is characterised in that the amino nitrogen is not bonded directly to the double bond, such as 2,5-dihydro-1-pyrrol-1-yl or 1,2,3,6-tetrahydro-1-pyridyl.

Lower alkadienyleneamino is e.g. a six-membered ring, e.g. 1,4-di-hydro-1-pyridyl, or preferably a five-membered ring which is of aromatic character, e.g. 1H-pyrrol-1-yl. One or two of the carbon atoms may be replaced by e.g. nitrogen thus resulting in e.g. 1H-triazol-1-yl, 1H-pyrazol-1-yl or preferably 1H-imidazol-1-yl radicals which may be substituted by the substituents indicated below for heterocyclic radicals or are advantageously unsubstituted.

To be mentioned as secondary or also as tertiary amino groups in this connection are also amino groups substituted by arylamino or arylimino groups, for example phenylhydrazino or phenylazo, or lower alkylamino or lower alkylimino groups, for example methylhydrazino or methylazo.

Acylamino is preferably lower-alkanoylamino, such as acetylamino, benzoylamino or phenyl-lower-alkanoylamino, both of which can be substituted in the phenyl ring for example with halogen, nitro, lower alkyl and/or lower alkoxy.

Di-acylamino is e.g. di-lower alkanoylamino, such as diacetylamino, or dibenzoylamino which optionally is substituted in the phenyl rings e.g. by halogen, lower alkyl, lower alkoxy and/or nitro.

Quaternary ammonium salts are derived from corresponding tertiary amino groups mentioned above, contain as quaternary substituent optionally substituted lower alkyl, for example lower alkyl, hydroxy- or halo-lower alkyl, phenyl-lower alkyl, phenoxy-lower alkyl or phenylthio-lower alkyl, wherein the phenyl moiety can in each case be unsubstituted or substituted by e.g. lower alkyl, lower alkoxy, halogen, trifluoromethyl and/or by nitro, and are preferably a tri-lower-alkylammonium salt, but also e.g. a phenyl-lower-alkyl-di-lower-alkylammonium salt or a phenoxy-lower-alkyl-di-lower-alkylammonium salt. They correspond to the salts defined hereinafter, especially the salts mentioned in particular as being pharmaceutically acceptable, non-toxic acid addition salts, and more especially those salts formed with hydrohalic acids, sulphuric or phosphoric acids.

Halogen is e.g. bromo or iodo, preferably fluoro and especially chloro.

Etherified hydroxy is in particular lower alkoxy or lower alkoxy substituted by e.g. halogen, hydroxy, amino, mono- or di-lower-alkylamino, epoxy or preferably by free or esterified carboxyl, e.g. (O-carboxymethyl)oxy or (O-ethoxycarbonylmethyl)oxy; further lower alkenyloxy, cycloalkyloxy, phenyloxy, phenyl-lower-alkoxy, heterocyclyloxy or heterocyclyl-lower alkoxy, such as pyridyl-oxy or -methoxy, furyloxy or -methoxy or thienyl-oxy or -methoxy.

Esterified hydroxy is preferably alkanoyloxy, especially lower alkanoyloxy, or benzoyloxy that optionally is substituted by hydroxy, lower alkoxy, halogen, lower alkyl and/or nitro; but can also be e.g. lower alkoxycarbonyloxy or N-lower alkylthiocarbamoyloxy.

Etherified mercapto is in particular unsubstituted or substituted lower-alkylthio, preferably by free or esterified carboxy, e.g. (S-carboxymethyl)-thio or (S-ethoxycarbonylmethyl)-thio, but also e.g. by halogen, e.g. trifluoromethylthio, hydroxy, amino, mono- or di-lower-alkylamino or epoxy; phenylthio or phenyl-lower-alkylthio, heterocyclylthio or heterocyclyl-lower alkylthio, e.g. 2-imidazolylthio or 2-imidazolylmethylthio.

Esterified mercapto is preferably lower alkylsulfonyloxy, e.g. methylsulfonyloxy, or optionally substituted phenylsulfonyloxy, but can also be e.g. lower alkanoylthio, thiocyanato or benzoylthio which is optionally substituted in the phenyl ring as described below.

Oxidized mercapto is for example phenylsulfinyl, phenyl-lower alkylsulfinyl, lower alkylsulfinyl, phenylsulfonyl, phenyl-lower alkylsulfonyl or lower alkylsulfonyl, wherein phenyl radicals can be unsubstituted or be substituted as described below.

Free or functionally modified carboxyl is for example carboxy, esterified carboxyl, especially lower-alkoxycarbonyl, such as methoxycarbonyl or ethoxycarbonyl; amidated carboxy, particularly carbamoyl which is free or mono- or disubstituted by lower alkyl, by di-lower-alkylamino-alkyl or by phenyl which is unsubstituted or for its part substituted e.g. by halogen, lower alkyl and/or lower alkoxy; and also the cyano group.

Free or functionally modified sulfo is, for example, sulfo (-SO$_3$H), esterified sulfo, e.g. lower alkoxysulfonyl, phenoxysulfonyl or phenyl-lower-alkoxysulfonyl, or amidated sulfo, such as optionally N-lower alkylated, N,N-dilower alkylated or N-phenylated sulfamoyl.

The acyl radicals of an aliphatic carboxylic acid are in particular acyl radicals of alkanecarboxylic acids, i.e. alkanoyl, especially lower-alkane-carboxylic acids or lower-alkanedicarboxylic acids, i.e. lower alkanoyl or carboxy-substituted lower alkanoyl, but also of lower-alkenecarboxylic acids or lower-alkenedicarboxylic acids, i.e. lower alkenoyl or carboxy-substituted lower alkenoyl, and also of substituted lower-alkanecarboxylic acids, for example substituted by halogen, i.e. halo-lower alkanoyl, such as trifluoroacetyl.

The acyl radicals of cycloaliphatic, cycloaliphatic-aliphatic, aromatic, aromatic-aliphatic carboxylic acids have, both for the ring and for the optionally present aliphatic part, the below-given meaning of the corresponding hydrocarbon radicals and are preferably cycloalkanoyl, benzoyl or phenyl-lower alkanoyl. They can also carry substituents, for example, hydroxy, halogen, lower alkyl and/or lower alkoxy.

An unsubstituted or substituted hydrocarbon radical is for example: an aliphatic, cycloaliphatic, cycloaliphatic-aliphatic, aromatic, aromatic-aliphatic, or heterocyclic-aliphatic radical.

An aliphatic hydrocarbon radical, which is unsubstituted or substituted, is especially alkyl and in particular lower alkyl, but may be also alkenyl or alkynyl, especially lower-alkenyl or lower-alkynyl.

Substituents of aliphatic hydrocarbon radicals are for example: free, esterified or etherified hydroxy, free or etherified mercapto, lower-alkylthio, lower alkylsulfinyl, halogen or nitro, also free or esterified carboxyl, cyano and/or formyl.

Lower alkyl is preferably methyl, but may be also e.g. ethyl, n-propyl, isopropyl, n-butyl, isobutyl, sec-butyl, tert-butyl, n-pentyl, isopentyl, neopentyl, n-hexyl, isohexyl or n-heptyl. Lower alkyl can also be substituted for example by nitro, hydroxy, halogen, especially fluoro, hydroxycyano, hydroxyamino, lower alkylthio, acyl, for example lower alkanoyl, such as acetylmethyl, or by free or esterified carboxy, preferably lower-alkoxycarbonyl, for example methoxycarbonylethyl; unsubstituted or substituted imino, such as free or esterified hydroxyimino, lower-alkylimino or unsubstituted or substituted phenylimino; acyloxyimino, e.g. acetyloxyiminomethyl, di-lower-alkylimmonio-lower-alkyl, e.g. dimethylimmoniomethyl, amino, mono- or di-lower-alkylamino or lower-alkyleneamino, for example pyrrolidino or piperidino. A further possible substituted lower alkyl group is the lower alkyl group substituted by a 2,2-di-lower-alkyl-4,6-dioxo-1,3-dioxan-5-ylidene group, such as (2,2-dimethyl-4,6-dioxo-1,3-dioxan-5-ylidene)-methyl.

Lower alkenyl is for example: vinyl, allyl, 1-propenyl, isopropenyl, 1- or 2-methallyl or 2- or 3-butenyl. Lower alkynyl is for example: propargyl or 2-butynyl. Lower alkenyl may be substituted by e.g. free or esterified carboxy, nitro, lower alkylsulfinyl, lower alkylsulfonyl, aryl or lower alkylthio. Lower alkynyl may be substituted by e.g. aryl or free or esterified carboxy.

An unsubstituted or substituted cycloaliphatic or cycloaliphatic-aliphatic radical is for example mono-, bi- or polycyclic cycloalkyl, cycloalkenyl or cycloalkyl-lower alkyl, cycloalkenyl-lower-alkyl, cycloalkyl-lower-alkenyl or cycloalkenyl-lower alkenyl, wherein the cycloalkyl radical contains up to 12, for example 3-8, particularly however 3-6, ring carbon atoms, whilst a cycloalkenyl radical has for example up to 12, preferably however 5-6, carbon atoms and one or two double bonds. The aliphatic part of a cycloaliphatic-aliphatic radical can contain up to 7, but preferably up to 4, carbon atoms. The stated cyclic radicals can be, if desired, mono-, di- or polysubstituted, in a manner analogous to that in the case of the aromatic radicals given below.

An unsubstituted or substituted aromatic hydrocarbon radical, i.e. aryl, is for example a monocyclic, bicyclic or polycyclic aromatic radical, such as the phenyl or naphthyl radical, which may optionally be substituted as described below for the rings A and B. An unsubstituted or substituted aromatic-aliphatic hydrocarbon is for example an aliphatic hydrocarbon radical carrying up to 3 mono-, bi- or polycyclic aromatic radicals, which may also be substituted. It is in particular phenyl-lower-alkyl, but also phenyl-lower-alkenyl or phenyl-lower-alkynyl. These radicals can, if desired, be mono-, di- or polysubstituted in the aromatic part as described below for the rings A and B and also in the aliphatic part as described above for aliphatic hydrocarbon radicals.

A heterocyclic radical as such or in a heterocyclic-aliphatic group, as well as "heterocyclyl" when referred to above or hereinafter in connection with organic groups or radicals, e.g. within expressions like heterocyclyloxy, heterocyclyl-lower alkoxy, heterocyclylthio, heterocyclyl-lower alkylthio, heterocyclylamino or heterocyclyl-lower alkylamino, is e.g. a monocyclic heterocyclic radical having 3 to 8, preferably 5 to 8 and advantageously 5 or 6 ring members, which is preferably bonded by a ring carbon atom to the moiety that it is joined with. A heterocyclic radical as a value of X is always bonded by a carbon atom to the 3-methylidene substituent of the flavanone moiety. It contains e.g. 0 to 4, preferably 1, 2 or 3 double bonds and is advantageously of aromatic character; in the latter case it is named "heteroaryl".

Usually "heterocyclyl" contains 1 to 4, identical or different, hetero atoms as ring members, especially nitrogen, oxygen and/or sulfur atoms. Preferred are aza-, oxa-, thia-, thiaza-, thiadiaza-, oxaza-, oxadiaza-, diaza-, triaza- or tetraza-monocycles. Monocyclic "heterocyclyl" may optionally contain e.g. 1 or 2, preferably 1, fused benzo rings.

Monocyclic five-membered heteroaryl is e.g. pyrryl, pyrazolyl, imidazolyl, triazolyl, tetrazolyl, furyl, thienyl, isoxazolyl, oxazolyl, oxadiazolyl, isothiazolyl, thiazolyl, or thiadiazolyl, while monocyclic six-membered heteroaryl is e.g. pyridyl, pyridazinyl, pyrimidinyl, pyrazinyl or triazinyl. Monocyclic heteroaryl fused with one benzo ring is e.g. indolyl, isoindolyl, benzimidazolyl, benzofuranyl, benzothienyl, benzothiazolyl, benzoxazolyl, quinolinyl or isoquinolinyl. Monocyclic five- or six-membered heterocyclyl being not of aromatic character is preferably the partially saturated corresponding heteroaryl, e.g. dihydropyrryl, such as 4,5-dihydro-3-pyrrolyl, dihydrooxazolyl, such as 4,5-dihydro-2-oxazolyl, or 1,2-dihydropyrimidinyl, such as 1,2-dihydro-4-pyrimidinyl or tetrahydro-triazinyl, such as tetrahydro-1,2,4-triazin-3-yl.

Heterocyclyl radicals are unsubstituted or may be substituted, such as mono- or poly-substituted, such as, especially, disubstituted by hydroxy, lower alkoxy, lower alkanoyloxy, halogen, mercapto, lower alkylthio, phenylthio, lower alkyl, hydroxy-lower alkyl, lower alkoxy-lower alkyl, carboxy-lower alkyl, optionally N-lower alkylated amino-lower alkyl, amino, lower alkylamino, di-lower alkylamino, lower alkyleneamino, aza-, oxa- or thia-lower alkyleneamino, or acylamino, such as lower alkanoylamino, carboxy, esterified carboxy, such as lower alkoxycarbonyl, optionally substituted carbamoyl, such as N-mono-or N,N-di-lower alkylated carbamoyl, cyano, sulfo or sulfamoyl; phenyl optionally substituted by lower alkyl, nitro, lower alkoxy and/or by halogen; cycloalkyl, nitro, oxo and/or oxido.

Phenyl radicals when referred to within expressions like phenyloxy, phenyl-lower alkoxy, phenylthio, phenyl-lower alkylthio, phenylamino, phenyl-lower alkylamino, benzoylthio, phenylsulfinyl, phenyl-lower alkylsulfinyl, phenylsulfonyl or phenyl-lower alkylsulfonyl are unsubstituted or may be substituted in exactly the same way as described above for heterocyclyl radicals, with the exception of oxo and oxido substituents which are not suitable in case of phenyl.

The rings A and B may optionally be substituted preferably by free, etherified or esterified hydroxy, such as hydroxy, lower alkoxy or lower alkanoyloxy; etherified mercapto, such as lower alkylthio; secondary or tertiary amino, such as lower alkylamino, di-lower alkylamino, lower alkyleneamino, aza-, oxa- or thia-lower alkyleneamino, or acylamino; lower alkyl; halogen; free or functionally modified carboxyl, such as carboxy, lower alkoxycarbonyl, carbamoyl, N-mono-or N,N-di-lower alkylacarbamoyl or cyano; nitro; or amidated sulfo, such as sulfamoyl, N-lower-alkyl-, N,N-di-lower-alkyl- or N-phenyl-sulfamoyl. Further substituents that come into consideration are e.g. amino, di-acylamino or sulfo, or methylenedioxy.

If the lower alkyl part of the radicals lower alkoxycarbonyl, lower alkoxy, lower alkylthio, lower alkylamino, di-lower alkylamino, N-lower alkyl- or N,N-di-lower alkylcarbamoyl and similar ones is substituted by hydroxy, mercapto, amino or lower alkylamino, methyl is not intended as a value of lower alkyl due to lacking stability of those compounds.

Cycloalkyl is e.g. cyclohexyl or cyclopropyl.

Lower alkoxy is e.g. methoxy, ethoxy, n-propoxy, isopropoxy, n-butoxy or tert.butoxy.

Lower alkylthio is for example methylthio, ethylthio, n-propylthio, isopropylthio, n-butylthio or tert-butylthio.

Lower alkenyloxy is for example vinyloxy or allyloxy.

Cycloalkyloxy is for example cyclopentyloxy, cyclohexyloxy, or also cyclopropyloxy or cycloheptyloxy.

Phenyl-lower alkoxy is for example benzyloxy, 2-phenylethoxy or di-phenylmethoxy.

Phenyl-lower alkylthio is for example benzylthio or 2-phenylethylthio.

Lower alkoxycarbonyloxy is for example methoxycarbonyloxy or ethoxycarbonyloxy.

Lower alkylthiocarbamoyloxy is for example N-methylthiocarbamoyloxy.

Alkanoyloxy is e.g. palmitoyloxy; lower alkanoyloxy represents for example formyloxy, acetoxy, propionyloxy, butyryloxy, isobutyryloxy, pivaloyloxy or valeroyloxy.

Lower alkanoylthio is for example formylthio, acetylthio, propionylthio, isobutyrylthio, pivaloylthio or valeroylthio.

Lower alkanoyl is e.g. formyl, acetyl, propionyl, n-butyryl, pivaloyl or valeroyl; alkanoyl is e.g. palmitoyl.

Carboxy-substituted lower alkanoyl is for example oxaloyl, malonoyl, succinoyl, glutaroyl or adipinoyl.

Lower alkenoyl is e.g. propenoyl (acryloyl), 2-butenoyl (crotonoyl) or 3-butenoyl.

Carboxy-substituted lower alkenoyl is e.g. maleinoyl or fumaroyl.

Cycloalkanoyl is preferably cyclo($C_3$-$C_8$)alkanoyl, such as cyclohexanoyl.

Lower alkylsulfinyl is for example methylsulfinyl, ethylsulfinyl, n-propylsulfinyl, isopropylsulfinyl, n-butylsulfinyl, isobutylsulfinyl or tert-butylsulfinyl.

Lower alkylsulfonyl is for example methylsulfonyl, ethylsulfonyl, n-propylsulfonyl, isopropylsulfonyl, n-butylsulfonyl, isobutylsulfonyl or tert-butylsulfonyl.

Phenylsulfonyloxy is optionally substituted in the phenyl part in a manner analogous to that in the case of the aromatic radicals given above, and is preferably phenylsulfonyloxy or p-toluenesulfonyloxy.

Phenyl-lower alkylsulfinyl is for example benzylsulfinyl or 2-phenylethylsulfinyl.

Phenyl-lower alkylsulfonyl is for example benzylsulfonyl or 2-phenylethylsulfonyl.

The compounds of the formula I possess valuable pharmacological properties. They, for example, stimulate the mucociliary transport in bronchia, and they modify the secretion of the viscoelasticity of mucus produced by bronchial and tracheal glands. These properties make the compounds useful for the treatment of diseases of the respiratory tract, as for example chronic bronchitis, in mammals.

The stimulation of mucociliary transport can be demonstrated with pharmacological model of frog oesophagus. In this system, the speed of transport of particles by the ciliated epithelium of frog oesophagus is measured according to Puchelle et al. [Bull. Physio. path. resp. 12, 771–779 (1976)].

By adding solutions of compounds to be tested on the frog oesophagus an increase in the speed of transport is measured. This effect appears when using solutions of compounds of formula I with a concentration of only $10^{-3}$–$10^{-4}$ M or less.

The relaxing effect of these compounds on the smooth muscles of bronchi can be demonstrated by the protection afforded by these compounds against the broncho-spasm induced by histamine aerosol in Guinea-pigs. Pretreatment of Guinea-pigs by i.p. route with compounds of formula I at a dose of 100 mg/kg or less allows the animals to resist more than 5 minutes to the histamine aerosol; control animals do not resist more than 1 minute and 30 sec.

The modification of viscoelasticity of mucus samples caused by compounds of formula I can be measured with a microrheometer according to C. Marriott [Advances in experimental Medicine and Biology, 144, 75–84 (1981)].

The mucus is obtained from fresh pig's stomach scrapings and is purified biochemically before use. The test compounds are dissolved in specific solvents, distilled water, phosphate buffer, methanol aqueous mixture, or in DMSO (dimethylsulfoxide). 50 mg aliquotes of mucus with 5–10 μl of the test solution are added. The samples are mixed, centrifuged and incubated for 30 min. for interaction to take place. The samples are then loaded into the cell of an oscillating sphere magnetic microrheometer and a 200 μm iron sphere is placed centerally in the sample which is allowed 5 minutes for relaxation to take place. The rheological behaviour is evaluated at 25° C. over the frequency range of 0.1 to 20 Hz. The elastic modulus G′ of mucus is changed, preferably reduced, but also enlarged, by using the compounds of formula I.

The mucoregulators properties of the compounds of formula I can be evaluated by the use of the "Ussing Chamber method" described in Respirat. Environ. Exercice Physiol. 49, 1027–1031 (1980).

In this method pieces of pig trachea are kept alive in physiological saline medium. The outlets of tracheal glands are observed via a light microscope. The mucus output is triggered either by electric stimulation or by addition of pilocarpine to the incubation medium. The number and the surface of mucus hillocks are recorded via a video tape recorder. The addition of the compounds of formula I in the incubation medium at a concentration of only $10^{-4}$ M or less modifies the number and the surface of hillocks reflecting a change in mucus secretion.

The compounds of formula I also have properties of preventing the hepatic necrosis and of immunomodulation.

The hepatic antinecrotic properties of these substances can be demonstrated by the galactosamine hepatitis test in the rat and the carbontetrachloride hepatitis test in the mouse. The galactosamine hepatitis in the rat is a well-known model to faithfully reproduce the morphological and biochemical changes of the human viral hepatitis [K. Decker et al., Adv. enzyme regul. 11, 205 (1973)].

Rats treated intraperitoneally or orally with doses of the compounds of formula I varying from 10 to 200 mg/kg are protected from the hepatic necrosis induced with galactosamine or carbontetrachloride. The hepatic effect is assessed by dosage of plasma transaminases and by measuring the sleeping time induced by pentobarbital which reflects liver function.

The immunomodulation properties of these substances can be demonstrated by a battery of tests classically used in immunology:

(a) humoral immunity test: production of antibodies against the bovine albumine in the mouse. Compounds of formula I, administered at a dose of 10 to 100 mg/kg, 15 minutes after the antigen (bovine albumine), stimulate the antibody production against this antigen, as measured 15 to 28 days later by the passive hemagglutination technique.

(b) cellular immunity test: delayed hypersensitivity reaction to sheep red blood cells in mice. Compounds of formula I administered at a dose of 10 to 100 mg/kg by subcutaneous route at the same time as the antigen stimulate the delayed hypersensitivity reaction triggered off 21 days later by a subcutaneous injection of the antigen.

(c) cytotoxicity test of mice macrophages against tumoral cells. The macrophages collected from mice having been treated by doses of 10 to 100 mg/kg of compounds of formula I, have a stimulated cytotoxicity against tumoral target cells.

These tests establish that the three main processes involved in the immunological defence (humoral immunity, cellular immunity and macrophages) are modified by the action of compounds of formula I and demonstrate their immunomodulating properties.

These various properties particularly designate the compounds of formula I for the treatment in mammals of acute and chronic diseases induced by viruses, toxins or alcohol. As a matter of fact, during these diseases, the impairment of the hepatic functions results essentially from the hepatic necrosis. This alterations can be diminished by the new substances.

The stimulation of the immunologic defences induced by these substances is useful for the treatment in mammals of the acute and chronic viral hepatitis and also for the treatment of all cases when there is an alteration of immunologic defence reactions such as repeating bacterial or viral infections or carcinogenous diseases. In the latter case, the interest of the substances is specifically demonstrated by the activation of cytotoxic effect of macrophages for tumoral cells.

Compounds of formula I are also able to diminish an increased microvascular permeability and therefore are very potent antioedamators agents in mammals.

Increased microvascular permeability with generalized oedema can be induced in rats by administration of galactosamine and dextran.

At doses administrated parenterally or orally varying from 10 to 500 mg/kg compounds of formula I prove to be able to reduce the oedema as measured by the reduction in the accumulation of $I^{125}$ labelled albumine in paws of animals which receive previously an i.v. injection of $I^{125}$ albumine. This measurement is an estimation of the micro-vascular permeability as reported by O. P. Gulati et al., Archives Int. de Pharmacodynamie et de Thérapie 263, pp. 272–287 (1983).

The invention relates especially to pharmaceutical preparations containing compounds of formula I, wherein X is primary, secondary or tertiary amino, acylamino, di-acylamino or a quaternary ammonium salt; halogen, hydroxy, unsubstituted or substituted lower-alkoxy, lower-alkenyloxy, cycloalkoxy, phenyloxy, phenyl-lower-alkoxy, heteroaryloxy or heteroaryl-lower-alkoxy, lower-alkoxycarbonyloxy, lower-alkylsulfonyloxy, phenylsulfonyloxy, lower-alkanoyloxy or benzoyloxy; mercapto, unsubstituted or substituted lower-alkylthio, phenylthio, phenyl-lower-alkylthio, heteroarylthio or heteroaryl-lower-alkylthio, lower-alkoxycarbonylthio or lower-alkanoylthio; unsubstituted or substituted phenylsulfinyl, phenyl-lower-alkylsulfinyl, lower alkylsulfinyl, phenyl-sulfonyl, phenyl-lower-alkylsulfonyl or lower alkylsulfonyl; free or esterified carboxyl, amidated carboxyl or cyano; sulfo; lower alkoxy-sulfonyl, phenyl-lower-alkoxysulfonyl or optionally N-lower alkylated, N,N-di-lower alkylated or N-phenylated sulfamoyl; unsubstituted or substituted lower alkanoyl, cycloalkanoyl, benzoyl or phenyl-lower-alkanoyl; nitro or a saturated or unsaturated, unsubstituted or substituted aliphatic, cycloaliphatic, cycloaliphatic-aliphatic, aromatic, aromatic-aliphatic, heterocyclic or heterocyclic-aliphatic radical; Y is oxygen, sulfur, sulfinyl or sulfonyl but must be oxygen, sulfinyl or sulfonyl, if X is 1H-imidazol-1-yl; and A and B are rings each unsubstituted or substituted by 1, 2, 3 or 4 substituents; or pharmaceutically acceptable salts of such compounds that contain a salt-forming group.

The invention relates more especially to pharmaceutical preparations containing compounds of formula I, wherein X is amino, unsubstituted or substituted lower-alkylamino, di-lower-alkylamino, cycloalkylamino, N-cycloalkyl-N-lower-alkylamino, phenylamino, N-phenyl-N-lower-alkylamino, phenyl-lower-alkylamino, N-phenyl-lower-alkyl-N-lower-alkylamino, lower alkyleneamino, aza-, oxa- or thia-lower-alkyleneamino, heteroarylamino, heteroaryl-lower-alkylamino, lower-alkanoyl-amino, benzoylamino, phenyl-lower-alkanoylamino or phenylhydrazino; a tri-lower-alkylammonium salt; hydroxy, unsubstituted or substituted lower-alkoxy, lower-alkenyloxy, phenyloxy, phenyl-lower-alkoxy, heteroaryloxy, heteroaryl-lower-alkoxy, lower alkoxycarbonyloxy, lower alkanoyloxy or benzoyloxy; mercapto, unsubstituted or substituted lower-alkylthio, phenylthio, phenyl-lower-alkylthio, heteroarylthio or heteroaryl-lower alkylthio; carboxy, lower-alkoxycarbonyl, optionally N-lower-alkylated, N,N-di-lower-alkylated or N-phenylated carbamoyl, or cyano; unsubstituted or substituted lower alkanoyl, benzoyl or phenyl-lower-alkanoyl; or an unsubstituted or substituted alkyl, alkenyl or alkynyl radical, unsubstituted or substituted cycloalkyl, cycloalkenyl, cycloalkyl-lower alkyl, cycloalkenyl-lower-alkyl, cycloalkyl-lower-alkenyl or cycloalkenyl-lower-alkenyl, or an unsubstituted or substituted phenyl or phenyl-lower-alkyl radical, or unsubstituted or substituted heteroaryl bonded by a carbon atom, or heteroaryl-lower alkyl; wherein the term "heteroaryl" is always defined as an aza-, thia-, oxa-, thiaza-, oxaza-, diaza-, triaza- or tetraza-monocycle of 3 to 8 ring members that optionally contains a fused benzo ring; Y is oxygen, sulfur, sulfinyl or sulfonyl; and A and B are rings each unsubstituted or substituted by 1, 2 or 3 substituents; or pharmaceutically acceptable salts of such compounds that contain a salt-forming group.

The invention relates most especially to pharmaceutical preparations containing compounds of formula I, wherein X is amino, a tri-lower-alkyl-ammonium salt, hydroxy, mercapto, carboxy, lower alkoxycarbonyl, carbamoyl, N-mono- or N,N-di-lower-alkylcarbamoyl, cyano or lower-alkoxycarbonyloxy;

or wherein X represents optionally substituted phenyl, phenylamino, phenylhydrazino, benzoylamino, phenyloxy, benzoyloxy, phenylthio, benzoyl, N-phenyl-N-lower-alkylamino, phenyl-lower-alkylamino, N-phenyl-lower-alkyl-N-lower-alkylamino, phenyl-lower-alkanoylamino, phenyl-lower-alkoxy, phenyl-lower-alkylthio, N-phenylcarbamoyl or phenyl-lower-alkanoyl, heteroarylamino, heteroaryl-lower alkylamino, heteroaryloxy, heteroaryl-lower alkoxy, heteroarylthio, heteroaryl-lower alkylthio, heteroaryl bonded by a carbon atom, or heteroaryl-lower alkyl, wherein the term "heteroaryl" is always defined as an aza-, thia-, oxa-, thiaza-, oxaza-, diaza-, triaza- or tetraza-monocycle of 3 to 8 ring members that optionally contains a fused benzo ring, in which radicals X the substituents optionally present are hydroxy, lower alkoxy, lower alkanoyloxy, lower alkylthio, amino, lower alkylamino, di-lower alkylamino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl, N-lower-alkyl-, N,N-di-lower-alkyl-or N-phenylsulfamoyl;

or wherein X represents unsubstituted or substituted lower alkylamino, di-lower alkylamino, cycloalkylamino, N-cycloalkyl-N-lower-alkylamino, lower alkyleneamino, aza-, oxa- or thia-lower alkyleneamino, lower alkanoylamino, lower alkoxy, lower alkenyloxy, lower alkanoyloxy, lower alkylthio or lower alkanoyl, in which radicals X the substitutents optionally present are hydroxy, lower alkoxy, lower alkanoyloxy, amino, lower alkylamino, di-lower-alkylamino, acylamino, di-acylamino, carboxy, lower alkoxycarbonyl, carbamoyl, N-mono- or N,N-di-lower-alkylcarbamoyl, cyano or phenyl that optionally is substituted by carboxy, lower alkoxycarbonyl or cyano;

or wherein X is an unsubstituted or substituted alkyl, alkenyl or alkynyl radical, unsubstituted or substituted cycloalkyl, cycloakenyl, cycloalkyl-lower-alkyl, cycloalkenyl-lower-alkyl, cycloalkyl-lower-alkenyl or cycloalkenyl-lower-alkenyl or an unsubstituted or substituted phenyl-lower-alkyl radical, in which radicals X the substituents optionally present are hydroxy, lower alkoxy, lower alkanoyloxy, halogen, mercapto, lower alkylthio, carboxy, lower alkoxycarbonyl, carbamoyl, N-mono- or N,N-di-lower alkylcarbamoyl, cyano, nitro, amino, lower alkylamino, di-lower-alkylamino, acylamino, diacylamino, lower alkyleneamino or phenyl;

Y is oxygen, sulfur, sulfinyl or sulfonyl, and A and B are rings each unsubstituted or substituted by 1, 2 or 3 substituents selected from the group consisting of hydroxy, lower alkoxy, lower alkanoyloxy, lower alkylthio, amino, lower alkylamino, di-lower alkylamino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl, N-lower-alkyl-, N,N-di-lower-alkyl- or N-phenylsulfamoyl; or pharmaceutically acceptable salts of such compounds that contain a salt-forming group.

The invention relates specifically to pharmaceutical preparations containing compounds of formula I, wherein X is amino, a tri-lower-alkylammonium salt, hydroxy, carboxy, lower alkoxycarbonyl, carbamoyl, N-mono-or N,N-di-lower-alkylcarbamoyl or cyano;

or wherein X represents optionally substituted phenyl, phenylamino, benzoylamino, phenyloxy, benzoyloxy, phenylthio, N-phenyl-N-lower-alkylamino, phenyl-lower-alkylamino, N-phenyl-lower-alkyl-N-lower-alkylamino, phenyl-lower-alkanoylamino, phenyl-lower-alkoxy, phenyl-lower-alkylthio, heteroarylamino, heteroaryloxy, heteroarylthio or heteroaryl bonded by a carbon atom, wherein the term "heteroaryl" is always defined as an aza-, thia-, oxa-, thiaza-, oxaza-, diaza-, triaza- or tetraza-monocycle of 5 or 6 ring members that optionally contains a fused benzo ring, in which radicals X the substituents optionally present are hydroxy, lower alkoxy, lower alkanoyloxy, lower alkylthio, lower alkylamino, di-lower alkylamino, acylamino, lower alkyl, halogen, carboxy, lower alkoxycarbonyl, carbamoyl, N-mono- or N,N-di-lower alkylcarbamoyl, cyano, nitro, sulfamoyl, N-lower-alkyl-, N,N-di-lower-alkyl- or N-phenylsulfamoyl;

or wherein X represents unsubstituted or substituted lower alkylamino, di-lower alkylamino, cycloalkylamino, N-cycloalkyl-N-lower-alkylamino, lower alkyleneamino, aza-, oxa- or thia-lower alkyleneamino, lower alkanoylamino, lower alkoxy, lower alkanoyloxy or lower alkylthio, in which radicals X the substituents optionally present are hydroxy, lower alkoxy, lower alkanoyloxy, di-lower-alkylamino, acylamino, carboxy, lower alkoxycarbonyl, carbamoyl, N-mono- or N,N-di-lower-alkylcarbamoyl or phenyl that optionally is substituted by carboxy, lower alkoxycarbonyl or cyano;

or wherein X is unsubstituted or substituted alkyl, cycloalkyl, cycloalkyl-lower-alkyl or phenyl-lower-alkyl, in which radicals X the substituents optionally present are hydroxy, lower alkoxy, lower alkanoyloxy, halogen, lower alkylthio, carboxy, lower alkoxycarbonyl, carbamoyl, N-mono- or N,N-di-lower-alkylcarbamoyl, cyano, nitro, di-lower-alkylamino, acylamino or lower alkyleneamino;

Y is oxygen, sulfur, sulfinyl or sulfonyl, and A and B are rings each unsubstituted or substituted by 1, 2 or 3 substituents selected from the group consisting of hydroxy, lower alkoxy, lower alkanoyloxy, lower alkylthio, lower alkylamino, di-lower alkylamino, acylamino, lower alkyl, halogen, carboxy, lower alkoxycarbonyl, carbamoyl, N-mono- or N,N-di-lower alkylcarbamoyl, cyano, nitro, sulfamoyl, N-lower-alkyl-, N,N-di-lower-alkyl- or N-phenylsulfamoyl; or pharmaceutically acceptable salts of such compounds that contain a salt-forming group.

The invention relates in particular to pharmaceutical preparations containing compounds of formula I, wherein X is amino, lower-alkylamino or di-lower-alkylamino the lower alkyl part being optionally substituted by carboxy, lower-alkoxycarbonyl, hydroxy or phenyl that optionally may be substituted itself by carboxy or lower-alkoxycarbonyl; lower alkyleneamino, phenylamino the phenyl part being optionally substituted by hydroxy, lower alkoxy, carbamoyl, N-mono- or N,N-di-lower-alkyl-carbamoyl, sulfo, sulfamoyl, N-mono- or N,N-di-lower-alkylsulfamoyl; lower alkanoylamino, hydroxy, lower alkoxy optionally substituted by carboxy or lower-alkoxy-carbonyl; lower alkylthio optionally substituted by carboxy or lower-alkoxycarbonyl; lower alkyl or phenyl that optionally may be substituted by lower-alkylamino, di-lower-alkylamino or lower-alkanoylamino; Y is oxygen, sulfur, sulfinyl or sulfonyl; and A and B are rings each unsubstituted, or mono- or disubstituted by hydroxy, halogen, lower alkyl, lower alkoxy, lower-alkylamino or di-lower-alkylamino, lower alkanoylamino, carboxy or lower-alkoxycarbonyl; or pharmaceutically acceptable salts of such compounds that contain a salt-forming group.

Further preferred are pharmaceutical preparations containing compounds of formula I, wherein X is hydroxy, Y is sulfur, A is phenylene unsubstituted oder substituted by 1 or 2 substituents selected from the group comprising halogen, lower alkyl, phenyl, phenyl-lower-alkyl, hydroxy, lower alkoxy and lower alkylthio, and B is phenyl unsubstituted or monosubstituted by halogen, hydroxy, lower alkoxy, lower alkyl, lower alkylthio, cyano or nitro; and/or containing a compound of formula I, wherein X is dimethylamino, Y is oxygen, A is phenylene and B is phenyl, or pharmaceutically acceptable salts of such compounds that contain a salt-forming group.

The invention also relates to compounds of formula I

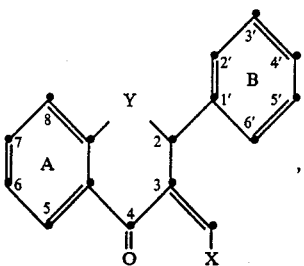

(I)

in which X represents unsubstituted or substituted amino or a quaternary ammonium salt; halogen, free, etherified or esterified hydroxy; free, etherified, esterified or oxidized mercapto; free or functionally modified carboxyl, free or functionally modified sulfo; acyl; nitro; an unsubstituted or substituted hydrocarbon radical or an unsubstituted or substituted heterocyclic radical, Y represents oxygen, sulfur, sulfinyl or sulfonyl, and rings A and B are each unsubstituted or substituted; with the provisos that Y must be oxygen, sulfinyl or sulfonyl, if X is 1H-imidazol-1-yl or hydroxy;

at least one of the rings A and B must be substituted, if Y is oxygen and X is hydroxy, chloro, dimethylamino or methylsulfonyloxy; and Y must be sulfur, sulfinyl or sulfonyl, if X is 2-phenylethenyl or 4-phenyl-1,3-butadienyl;

Y must be oxygen or sulfinyl, if A is 6-methyl-1,2-phenylene and X is phenyl or 4-methoxyphenyl;

Y must be sulfur, sulfinyl or sulfonyl, if A is 6-nitro-1,2-phenylene and X is optionally substituted phenyl, or naphth-1-yl;

Y must be sulfur, sulfinyl or sulfonyl, if A is 1,2-phenylene and X is phenyl, 4-methoxyphenyl, 4-N,N-di-lower-alkylaminophenyl, 3- or 4-hydroxyphenyl, 2- or 4-nitrophenyl, 4-halophenyl, 3-methoxy-4-acetoxyphenyl, 4-lower-alkylphenyl, 4-acetylaminophenyl, 4-cyanophenyl, dihalophenyl, 1,3-benzodioxol-5-yl or 4-hydroxy-3,5-di(C$_1$–C$_4$)alkylphenyl;

Y must be sulfur, sulfinyl or sulfonyl, if ring A is substituted and ring B is unsubstituted and X is phenyl, 4-aminophenyl, 4-methoxyphenyl or 3,4-dimethoxyphenyl;

and salts of such compounds that contain a salt-forming group.

Preferred are compounds of formula I, wherein X is primary, secondary or tertiary amino, acylamino, diacylamino or a quaternary ammonium salt; halogen, hydroxy, unsubstituted or substituted lower-alkoxy, lower-alkenyloxy, cycloalkoxy, phenyloxy, phenyl-lower-alkoxy, heteroaryloxy or heteroaryl-lower-alkoxy, lower-alkoxycarbonyloxy, lower-alkylsulfonyloxy, phenylsulfonyloxy, lower-alkanoyloxy or benzoyloxy; mercapto, unsubstituted or substituted lower-alkylthio, phenylthio, phenyl-lower-alkylthio, heteroarylthio or heteroaryl-lower-alkylthio, lower-alkoxycarbonylthio or lower-alkanoylthio; unsubstituted or substituted phenylsulfinyl, phenyl-lower-alkylsulfinyl, lower alkylsulfinyl, phenyl-sulfonyl, phenyl-lower-alkylsulfonyl or lower alkylsulfonyl; free or esterified carboxyl, amidated carboxyl or cyano; sulfo; lower alkoxy-sulfonyl, phenyl-lower-alkoxysulfonyl or optionally N-lower alkylated, N,N-di-lower alkylated or N-phenylated sulfamoyl; unsubstituted or substituted lower alkanoyl, cycloalkanoyl, benzoyl or phenyl-lower-alkanoyl; nitro or a saturated or unsaturated, unsubstituted or substituted aliphatic, cycloaliphatic, cycloaliphatic-aliphatic, aromatic-aliphatic, heterocyclic or heterocyclic-aliphatic radical; Y is oxygen, sulfur, sulfinyl or sulfonyl; and A and B are rings each unsubstituted or substituted by 1, 2, 3 or 4 substituents; with the provisos that Y must be oxygen, sulfinyl or sulfonyl, if X is 1H-imidazol-1-yl or hydroxy;

at least one of the rings A and B must be substituted, if Y is oxygen and X is hydroxy, chloro, dimethylamino or methylsulfonyloxy; and Y must be sulfur, sulfinyl or sulfonyl, if X is 2-phenylethenyl or 4-phenyl-1,3-butadienyl;

and salts of such compounds that contain a salt-forming group.

Especially preferred are compounds of formula I, wherein X is amino, unsubstituted or substituted lower-alkylamino, di-lower-alkylamino, cycloalkylamino, N-cycloalkyl-N-lower-alkylamino, phenylamino, N-phenyl-N-lower-alkylamino, phenyl-lower-alkylamino, N-phenyl-lower-alkyl-N-lower-alkylamino, lower alkyleneamino, aza-, oxa-or thia-lower-alkyleneamino, heteroarylamino, heteroaryl-lower-alkylamino, lower-alkanoylamino, benzoylamino, phenyl-lower-alkanoylamino or phenylhydrazino; a tri-lower-alkylammonium salt; halogen, unsubstituted or substituted lower-alkoxy, lower-alkenyloxy, phenyloxy, phenyl-lower-alkoxy, heteroaryloxy, heteroaryl-lower alkoxy, lower alkoxycarbonyloxy, lower alkanoyloxy or benzoyloxy; mercapto, unsubstituted or substituted lower-alkylthio, phenylthio, phenyl-lower-alkylthio, heteroarylthio or heteroaryl-lower alkylthio; carboxy, lower-alkoxycarbonyl, optionally N-lower-alkylated, N,N-di-lower-alkylated or N-phenylated carbamoyl, or cyano; unsubstituted or substituted lower alkanoyl, benzoyl or phenyl-lower-alkanoyl; or an unsubstituted or substituted alkyl or alkynyl radical, an alkenyl radical, which is unsubstituted or substituted by hydroxy, lower alkoxy, lower alkanoyloxy, halogen, mercapto, lower alkylthio, lower alkylsulfinyl, lower alkylsulfonyl, carboxy, lower alkoxy-carbonyl, carbamoyl, N-mono- or N,N-di-lower alkylcarbamoyl, cyano, nitro, amino, lower alkylamino, di-lower alkylamino, acylamino, diacylamino or lower alkyleneamino; unsubstituted or substituted cycloalkyl, cycloalkenyl, cycloalkyl-lower-alkyl, cycloalkenyl-lower-alkyl, cycloalkyl-lower-alkenyl or cycloalkenyl-lower-alkenyl, or an unsubstituted or substituted phenyl-lower-alkyl radical, or unsubstituted or substituted heteroaryl bonded by a carbon atom, or heteroaryl-lower alkyl; wherein the term "heteroaryl" is always defined as an aza-, thia-, oxa-, thiaza-, oxaza-, diaza-, triaza- or tetraza-monocycle of 3 to 8 ring members that optionally contains a fused benzo ring; Y is oxygen, sulfur, sulfinyl or sulfonyl; and A and B are rings each unsubstituted or substituted by 1,2 or 3 substituents;

with the proviso that at least one of the rings A and B is substituted, if Y is oxygen and X is chloro or dimethylamino, and pharmaceutically acceptable salts of such compounds that contain a salt-forming group.

A preferred embodiment of this invention relates to compounds of formula I, in which Y is oxygen, X is amino, unsubstituted or substituted lower-alkylamino, N-(C$_1$–C$_7$)-alkyl-N-(C$_2$–C$_7$)-alkylamino, cycloalkylamino, N-cycloalkyl-N-lower-alkylamino, phenylamino, N-phenyl-N-lower-alkylamino, phenyl-loweralkylamino, N-phenyl-lower-alkyl-N-lower-alkylamino, lower alkyleneamino, aza-, oxa- or thia-lower-alkyleneamino, heteroarylamino, heteroaryl-lower alkylamino, lower-alkanoylamino, benzoylamino, phenyl-lower-alkanoylamino or phenyl-hydrazino; a tri-lower-alkylammonium salt; fluoro, bromo, iodo, unsubstituted or substituted lower-alkoxy, lower-alkenyloxy, phenyloxy, phenyl-lower-alkoxy, heteroaryloxy, heteroaryl-lower alkoxy, lower alkoxycarbonyloxy, lower alkanoyloxy or benzoyloxy; mercapto, unsubstituted or substituted lower-alkylthio, phenylthio, phenyl-lower-alkylthio, heteroarylthio or heteroaryl-lower alkylthio; carboxy, lower-alkoxycarbonyl, optionally N-lower-alkylated, N,N-di-lower-alkylated or N-phenylated carbamoyl, or cyano; unsubstituted or substituted lower alkanoyl, benzoyl or phenyl-lower-alkanoyl; or an unsubstituted or substituted alkyl or alkynyl radical, an alkenyl radical which is unsubstituted or substituted by hydroxy, lower alkoxy, lower alkanoyloxy, halogen, mercapto, lower alkylthio, lower alkylsulfinyl, lower alkylsulfonyl, carboxy, lower alkoxy-carbonyl, carbamoyl, N-mono- or N,N-di-lower alkylcarbamoyl, cyano, nitro, amino, lower alkylamino, di-lower alkylamino, acylamino, diacylamino or lower alkyleneamino; unsubstituted or substituted cycloalkyl, cycloalkenyl, cycloalkyl-lower-alkyl, cycloalkenyl-lower-alkyl, cycloalkyl-lower-alkenyl or cycloalkenyl-lower-alkenyl, or an unsubstituted or substituted phenyl-lower-alkyl radical or unsubstituted or substituted heteroaryl bonded by a carbon atom, or heteroaryl-lower alkyl; wherein the term "heteroaryl" is always defined as an aza-, thia-, oxa-, thiaza-, oxaza-, diaza-, triaza- or tetraza-monocycle of 3 to 8 ring members that optionally contains a fused benzo ring; and A and B are rings each unsubstituted or substituted by 1,2 or 3 substituents; or in which Y is sulfur, sulfinyl or sulfonyl; X is amino, unsubstituted or substituted lower-alkylamino, di-lower-alkylamino, cycloalkylamino, N-cycloalkyl-N-lower-alkylamino, phenylamino, N-phenyl-N-lower-alkylamino, phenyl-lower-alkylamino, N-phenyl-lower-alkyl-N-lower-alkylamino, lower alkyleneamino, aza-, oxa- or thia-lower-alkyleneamino, heteroarylamino, heteroaryl-lower alkylamino, lower-alkanoylamino, benzoylamino, phenyl-lower-alkanoylamino or phenyl-hydrazino; a tri-lower-alkylammonium salt; halogen, unsubstituted or substituted lower-alkoxy, lower-alkenyloxy, phenyloxy, phenyl-lower-alkoxy, heteroaryloxy, heteroaryl-lower alkoxy, lower alkoxycarbonyloxy, lower alkanoyloxy or benzoyloxy; mercapto, unsubstituted or substituted lower-alkylthio, phenylthio, phenyl-lower-alkylthio, heteroarylthio or heteroaryl-lower alkylthio; carboxy, lower-alkoxycarbonyl, optionally N-lower-alkylated, N,N-di-lower-alkylated or N-phenylated carbamoyl, or cyano; unsubstituted or substituted lower alkanoyl, benzoyl or phenyl-lower-alkanoyl; or an unsubstituted or substituted alkyl, alkenyl or alkynyl radical, unsubstituted or substituted cycloalkyl, cycloalkenyl, cycloalkyl-lower-alkyl, cycloalkenyl-lower-alkyl, cycloalkyl-lower-alkenyl or cycloalkenyl-lower alkenyl, or an unsubstituted or substituted phenyl-lower-alkyl radical or unsubstituted or substituted heteroaryl bonded by a carbon atom, or heteroaryl-lower alkyl; wherein the term "heteroaryl" is always defined as an aza-, thia-, oxa-, thiaza-, oxaza-, diaza-, triaza- or tetraza-monocycle of 3 to 8 ring members that optionally contains a fused benzo ring; and A and B have the meaning as given above, and pharmaceutically acceptable salts of such compounds that contain a salt-forming group.

Particularly preferred are the compounds of formula I, wherein X is amino, a tri-lower-alkylammonium salt, halogen, mercapto, carboxy, lower alkoxy-carbonyl, carbamoyl, N-mono- or N,N-di-lower-alkylcarbamoyl, cyano or lower-alkoxycarbonyloxy;

or wherein X represents optionally substituted phenylamino, phenyl-hydrazino, benzoylamino, phenyloxy, benzoyloxy, phenylthio, benzoyl, N-phenyl-N-lower-alkylamino, phenyl-lower-alkylamino, N-phenyl-lower-alkyl-N-lower-alkylamino, phenyl-lower-alkanoylamino, phenyl-lower-alkoxy, phenyl-lower-alkylthio, N-phenyl-carbamoyl or phenyl-lower-alkanoyl, heteroarylamino, heteroaryl-lower alkylamino, heteroaryloxy, heteroaryl-lower alkoxy, heteroarylthio, heteroaryl-lower alkylthio, heteroaryl bonded by a carbon atom, or heteroaryl-lower alkyl, wherein the term "heteroaryl" is always defined as an aza-, thia-, oxa-, thiaza-, oxaza-, diaza-, triaza- or tetraza-monocycle of 3 to 8 ring members that optionally contains a fused benzo ring, in which radicals X the substituents optionally present are hydroxy, lower alkoxy, lower alkanoyloxy, lower alkylthio, amino, lower alkylamino, di-lower alkylamino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl, N-lower-alkyl-, N,N-di-lower-alkyl-or N-phenylsulfamoyl;

or wherein X represents unsubstituted or substituted lower alkylamino, di-lower alkylamino, cycloalkylamino, N-cycloalkyl-N-lower-alkylamino, lower alkyleneamino, aza-, oxa- or thia-lower alkyleneamino, lower alkanoylamino, lower alkoxy, lower alkenyloxy, lower alkanoyloxy, lower alkylthio or lower alkanoyl, in which radicals X the substitutents optionally present are hydroxy, lower alkoxy, lower alkanoyloxy, amino, lower alkylamino, di-lower-alkylamino, acylamino, di-acylamino, carboxy, lower alkoxy-carbonyl, carbamoyl, N-mono- or N,N-di-lower-alkylcarbamoyl, cyano or phenyl that optionally is substituted by carboxy, lower alkoxycarbonyl or cyano;

or wherein X is an unsubstituted or substituted alkyl, alkenyl or alkynyl radical, unsubstituted or substituted cycloalkyl, cycloalkenyl, cycloalkyl-lower-alkyl, cycloalkenyl-lower-alkyl, cycloalkyl-lower-alkenyl or cycloalkenyl-lower-alkenyl or an unsubstituted or substituted phenyl-lower-alkyl radical, in which radicals X the substituents optionally present are hydroxy, lower alkoxy, lower alkanoyloxy, halogen, mercapto, lower alkylthio, carboxy, lower alkoxycarbonyl, carbamoyl, N-mono- or N,N-di-lower alkylcarbamoyl, cyano, nitro, amino, lower alkylamino, di-lower-alkylamino, acylamino, diacylamino or lower alkyleneamino;

Y is oxygen, sulfur, sulfinyl or sulfonyl, and A and B are rings each unsubstituted or substituted by 1,2 or 3 substituents selected from the group consisting of hydroxy, lower alkoxy, lower alkanoyloxy, lower alkylthio, amino, lower alkylamino, di-lower alkylamino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl or N-lower-alkyl-, N,N-di-lower-alkyl- or N-phenylsulfamoyl; with the proviso that at least one of the rings A and B is substituted, if Y is oxygen and X is chloro or dimethylamino; and pharmaceutically acceptable salts of such compounds that contain a salt-forming group.

Greatly preferred are the compounds of formula I, wherein X is amino, a tri-lower-alkylammonium salt, halogen, carboxy, lower alkoxycarbonyl, carbamoyl, N-mono- or N,N-di-lower-alkylcarbamoyl or cyano;

or wherein X represents optionally substituted phenylamino, benzoylamino, phenyloxy, benzoyloxy, phenylthio, N-phenyl-N-lower-alkylamino, phenyl-lower-alkylamino, N-phenyl-lower-alkyl-N-lower-alkylamino, phenyl-lower-alkanoylamino, phenyl-lower-alkoxy, phenyl-lower-alkylthio, heteroarylamino, heteroaryloxy, heteroarylthio or heteroaryl bonded by a carbon atom, wherein the term "heteroaryl" is always defined as an aza-, thia-, oxa-, thiaza-, oxaza-, diaza-, triaza- or tetraza-monocycle of 5 or 6 ring members that optionally contains a fused benzo ring, in which radicals X the substituents optionally present are hydroxy, lower alkoxy, lower alkanoyloxy, lower alkylthio, lower alkylamino, di-lower alkylamino, acylamino, lower alkyl, halogen, carboxy, lower alkoxycarbonyl, carbamoyl, N-mono- or N,N-di-lower alkylcarbamoyl, cyano, nitro, sulfamoyl, N-lower-alkyl-, N,N-di-lower-alkyl- or N-phenyl-sulfamoyl;

or wherein X represents unsubstituted or substituted lower alkylamino, di-lower alkylamino, cycloalkylamino, N-cycloalkyl-N-lower-alkylamino, lower alkyleneamino, aza-, oxa- or thia-lower alkyleneamino, lower alkanoylamino, lower alkoxy, lower alkanoyloxy or lower alkylthio, in which radicals X the substituents optionally present are hydroxy, lower alkoxy, lower alkanoyloxy, di-lower-alkylamino, acylamino, carboxy, lower alkoxycarbonyl, carbamoyl, N-mono- or N,N-di-lower-alkylcarbamoyl, or phenyl that optionally is substituted by carboxy, lower alkoxycarbonyl or cyano;

or wherein X is unsubstituted or substituted alkyl, cycloalkyl, cycloalkyl-lower-alkyl or phenyl-lower-alkyl, in which radicals X the substituents optionally present are hydroxy, lower alkoxy, lower alkanoyloxy, halogen, lower alkylthio, carboxy, lower alkoxycarbonylk, carbamoyl, N-mono- or N,N-di-lower-alkylcarbamoyl, cyano, nitro, di-lower-alkylamino, acylamino or lower alkyleneamino;

Y is oxygen, sulfur, sulfinyl or sulfonyl, and A and B are rings each unsubstituted or substituted by 1, 2 or 3 substituents selected from the group consisting of hydroxy, lower alkoxy, lower alkanoyloxy, lower alkylthio, lower alkylamino, di-lower alkylamino, acylamino, lower alkyl, halogen, carboxy, lower alkoxycarbonyl, carbamoyl, N-mono- or N,N-di-lower alkylcarbamoyl, cyano, nitro, sulfamoyl, N-lower-alkyl-, N,N-di-lower-alkyl-or N-phenylsulfamoyl; with the proviso that at least one of the rings A and B is substituted, if Y is oxygen and X is chloro or di-methylamino; and pharmaceutically acceptable salts of such compounds that contain a salt-forming group.

A particularly preferred embodiment of the invention is represented by compounds of formula I, wherein X is amino, lower-alkylamino or N-($C_1$–$C_7$)-alkyl-N-($C_2$–$C_7$)-alkylamino the alkyl part being optionally substituted by carboxy, lower-alkoxycarbonyl, hydroxy or phenyl that optionally may be substituted itself by carboxy or lower-alkoxycarbonyl; lower alkyleneamino; phenylamino the phenyl part being optionally substituted by hydroxy, lower alkoxy, carbamoyl, N-mono- or N,N-di-lower-alkylcarbamoyl, sulfo, sulfamoyl, N-mono- or N,N-di-lower-alkylsulfamoyl; lower-alkanoylamino, lower alkoxy optionally substituted by carboxy or lower-alkoxycarbonyl; lower alkylthio optionally substituted by carboxy or lower-alkoxycarbonyl; lower alkyl; Y is oxygen, sulfur, sulfinyl or sulfonyl; and A and B are rings each unsubstituted, or mono- or di-substituted by hydroxy, halogen, lower alkyl, lower alkoxy, lower-alkylamino or di-lower-alkylamino, lower alkanoylamino, carboxy or lower alkoxycarbonyl; and pharmaceutically acceptable salts of such compounds that contain a salt-forming group.

Further preferred are compounds of formula I, wherein X is dimethylamino, chloro or hydroxy, Y is oxygen and A and B are aromatic rings of which at least one is mono- or disubstituted by hydroxy, halogen, lower alkyl, lower alkoxy, lower-alkylamino, di-lower alkylamino, lower alkanoylamino, carboxy or lower alkoxy-carbonyl; and pharmaceutically acceptable salts of such compounds that contain a salt-forming group.

Further preferred are compounds of formula I, wherein X is dimethylamino or chloro, Y is sulfur, sulfinyl or sulfonyl, and A and B are rings each unsubstituted, or mono- or disubstituted by hydroxy, halogen, lower alkyl, lower alkoxy, lower alkylamino, di-lower alkylamino, lower alkanoylamino, carboxy or lower alkoxycarbonyl; and pharmaceutically acceptable salts of such compounds that contain a salt-forming group.

Another preferred embodiment of the invention is represented by compounds of formula I, wherein Y is oxygen, A and B are rings each unsubstituted or substituted by 1, 2 or 3 substituents selected from the group consisting of hydroxy, lower alkoxy, lower alkanoyloxy, amino, lower alkylamino, di-lower alkylamino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl, N-lower-alkyl-, N,N-di-lower-alkyl-or N-phenylsulfamoyl;

and X is phenyl which is mono-substituted by ethyl, n-propyl, n-butyl, isobutyl, sec.-butyl, ($C_5$–$C_7$)alkyl, iodo, ($C_3$–$C_7$)alkoxy, lower alkylamino, N-lower-alkyl-N-($C_3$–$C_7$)alkylamino, N-methyl-N-ethylamino, ($C_2$–$C_7$)alkylcarbonylamino, lower alkanoyloxy, carboxy, lower alkoxy-carbonyl, carbamoyl, N-mono- or N,N-di-lower alkylcarbamoyl, sulfamoyl, N-mono- or N,N-di-lower alkylsulfamoyl;

or X is phenyl mono-substituted in 2- or 3-position by methyl, isopropyl, tert.-butyl, chloro, bromo, amino, dimethylamino, diethylamino, acetylamino or cyano; or X is phenyl mono-substituted in the 3-position by nitro or methoxy, or in the 2-position by hydroxy, or in the 3- or 4-position by ethoxy;

or X is phenyl di-substituted by two substituents selected from the group comprising fluoro, bromo, iodo, ($C_2$–$C_7$)alkoxy, lower alkyl, ($C_2$–$C_7$)alkylcarbonyloxy, amino, lower alkylamino, di-lower alkylamino, lower alkanoylamino, carboxy, lower alkoxycarbonyl, carbamoyl, N-mono- or N,N-di-lower alkylcarbamoyl, cyano, nitro, sulfamoyl or N-mono-or N,N-di-lower alkylsulfamoyl;

or X is tri- or tetrasubstituted by 3 or 4 substituents selected from the group comprising lower alkoxy, lower alkanoyloxy, amino, lower alkylamino, di-lower alkylamino, lower alkanoylamino, lower alkyl, halogen, carboxy, lower alkoxycarbonyl, carbamoyl, N-mono- or N,N-di-lower alkylcarbamoyl, cyano, nitro, sulfamoyl or N-mono- or N,N-di-lower alkylsulfamoyl; and pharmaceutically acceptable salts of such compounds that contain a salt-forming group.

Also preferred are the compounds of formula I, wherein Y is sulfur, sulfinyl or sulfonyl, A and B are rings each unsubstituted or substituted by 1, 2 or 3 substituents selected from the group consisting of hydroxy, lower alkoxy, lower alkanoyloxy, amino, lower alkylamino, di-lower alkylamino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl or N-lower-alkyl-, N,N-di-lower-alkyl-or N-phenylsulfamoyl; and X is phenyl mono-substituted by hydroxy, ($C_2$–$C_7$)alkoxy, lower alkanoyloxy, amino, lower alkylamino, di-lower alkyl-amino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl or N-lower-alkyl-, N,N-di-lower-alkyl-or N-phenylsulfamoyl; or X is phenyl di-, tri- or tetrasubstituted by 2, 3 or 4 substituents selected from the group comprising hydroxy, lower alkoxy, lower alkanoyloxy, amino, lower alkylamino, di-lower alkylamino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl or N-lower-alkyl-, N,N-di-lower-alkyl-or N-phenylsulfamoyl; and pharmaceutically acceptable salts of such compounds that contain a salt-forming group.

Greatly preferred are the compounds of formula I, wherein Y is oxygen and X is phenyl substituted by lower alkanoylamino in 2- or 3-position or wherein Y is sulfur and X is phenyl substituted by lower alkanoylamino, and A and B are rings each unsubstituted or substituted by 1 or 2 substitutents selected from the group comprising hydroxy, lower alkoxy, lower alkanoyloxy, lower alkylthio, lower alkylamino, di-lower alkylamino, acylamino, lower alkyl, halogen, carboxy, lower alkoxycarbonyl, carbamoyl, N-mono- or N,N-di-lower alkylcarbamoyl, cyano, nitro, sulfamoyl, N-lower-alkyl-, N,N-di-lower-alkyl- or N-phenylsulfamoyl; and pharmaceutically acceptable salts of such compounds that contain a salt-forming group.

Further preferred are compounds of formula I, wherein X is lower alkadienyleneamino, Y is oxygen, sulfinyl or sulfonyl, and A and B are rings each unsubstituted or substituted, and pharmaceutically acceptable salts thereof.

In general, preferred are those compounds of formula I wherein Y is oxygen or sulfur.

The compounds specifically preferred are: 3-N,N-dimethylaminomethylidene-thioflavanone, 5-hydroxy-3-N,N-dimethylaminomethylidene-flavanone, 3-N,N-dimethylaminomethylidene-6-methyl-thioflavanone, 3-N,N-dimethylaminomethylidene-6-fluoro-flavanone, 6-N,N-dimethylamino-3-N,N-dimethylaminomethylidene-flavanone, 3-N,N-dimethylaminomethylidene-6-ethoxycarbonyl-flavanone, 3-N,N-dimethylaminomethylidene-7-methoxy-flavanone, 3-N,N-dimethylaminomethylidene-7-ethoxy-flavanone, 3-N,N-dimethylaminomethylidene-7-isopropyloxy-flavanone, 7-N,N-dimethylamino-3-N,N-dimethylaminomethylidene-flavanone, 7-acetylamino-3-N,N-dimethylaminomethylidene-flavanone, 3-N,N-dimethylaminomethylidene-7-fluoro-flavanone, 3-N,N-dimethylaminomethylidene-4'-hydroxy-flavanone, 3-N,N-dimethylaminomethylidene-4'-ethoxy-flavanone, 5,7-dimethoxy-3-N,N-dimethylaminomethylidene-flavanone, 3-hydroxymethylidene-6-methyl-thioflavanone, 3-(N-carboxymethyl)aminomethylidene-6-methyl-thioflavanone, 3-(N-2-hydroxyphenyl)aminomethylidene-6-methyl-thioflavanone, 3-(N-4-sulfamoylphenyl)aminomethylidene-6-methyl-thioflavanone, 3-ethylidene-6-methyl-thioflavanone, 3-isopropyloxy-methylidene-flavanone, 3-(N-carboxymethyl)aminomethylidene-flavanone, 3-(S-ethoxycarbonylmethyl)thiomethylidene-flavanone, 3-ethoxy-methylidene-6-methyl-thioflavanone, 3-(N-methoxycarbonylmethyl)aminomethylidene-6-methyl-thioflavanone, 3-(N-ethoxycarbonylmethyl)aminomethylidene-6-methyl-thioflavanone, 3-(O-ethoxycarbonylmethyl)oxymethylidene-6-methyl-thioflavanone, 3-(O-ethoxycarbonylmethyl)oxymethylidene-flavanone, 3-hydroxymethylidene-thioflavanone, 3-(N-methyl-N-ethoxycarbonylmethyl)aminomethylidene-6-methyl-thioflavanone, 3-(N-2-hydroxyphenyl)aminomethylidene-flavanone, 3-ethylidene-flavanone, 3-N-pyrrolidinomethylidene-flavanone, 3-N-isopropylaminomethylidene-flavanone, 3-N,N-di(2-hydroxyethyl)aminomethylidene-flavanone and 3-(1-imidazolyl)methylidene-flavanone, and pharmaceutically acceptable salts of such compounds that contain a salt-forming group.

Above all are preferred the compounds of formula I described in the examples and pharmaceutically acceptable salts thereof.

The invention also relates to pharmaceutical preparations containing the novel compounds of formula I or any of the preferred embodiments thereof as described above.

Compounds of the formula I can be produced by processes known per se.

The novel compounds of the formula I, and salts thereof, can be produced e.g. by replacing in the 3-position of a flavanone or thioflavanone compound of formula II

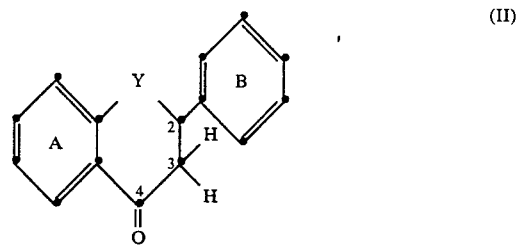

in which A, B and Y have the meanings defined in the formula I, two hydrogen atoms by a monosubstituted methylidene group, =CHX, in which X has the meaning defined in the formula I, and, if desired, converting a resulting compound of this formula I into another compound of the formula I according to the invention and/or, if desired, converting a free compound obtained into a salt, or a salt into the free compound or into another salt, and, if required, resolving a mixture of isomers or racemates obtained into the single isomers or racemates, and, if required, resolving a racemate obtained into the optical antipodes.

Two hydrogen atoms in the 3-position of the compounds of the formula II can be replaced in a manner known per se, for example by unsubstituted or substituted aminomethylidene or hydroxymethylidene or by methylidene substituted with a hydrocarbon radical. The replacement of the two hydrogen atoms in the 3-position by an unsubstituted or substituted aminomethylidene group can be effected for example (a) by the reaction of a compound of the formula II with a compound of the formula III

 (III), wherein R' and R'' are hydrogen, lower alkyl or unsubstituted or substituted phenyl, and R''' is lower alkyl, such as methyl or ethyl, or benzyl according to J. Org. Chem., Vol. 43, pp. 4248–4250, (1978);

(b) by reacting a compound of the formula II with "Gold's reagent", [3-(dimethylamino)-2-azaprop-2-en-1-ylidene]dimethylammonium chloride, according to J. Org. Chem., Vol. 45, pp. 4522–4524, (1980);

(c) by reaction of a compound of the formula II with an alkoxy-bis-(dimethylamino)methane of the formula IV

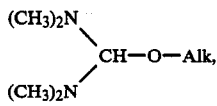 (IV)

in which Alk is lower alkyl, as for example tert-butyl, according to J. Amer. Chem. Soc., Vol. 98, pp. 7868–7869, (1976);

(d) by reacting a compound of the formula II with s-triazine and a secondary amine, especially a di-lower alkylamine or a lower alkyleneamine, e.g. piperidine, or oxa- or thia-lower alkyleneamine, e.g. morpholine, or thiomorpholine, according to Tetrahedron, Vol. 32, pp. 2603–2605, (1976); or (e) by reaction of a compound of the formula II with an orthoformic acid ester, HC(O-Alk)₃, in which Alk is lower alkyl, such as triethyl orthoformate and an arylamine, especially a phenylamine, such as aniline, to yield a compound of the formula I, wherein X is arylamino, e.g. phenylamino, according to Synthesis 1976, pp. 543.

The exchange of the two hydrogen atoms in the 3-position of a compound of the formula II by hydroxymethylidene can be performed e.g. with ethylformate in the presence of a base, such as sodium ethoxide, according to J. Med. Chem., Vol. 24, pp. 468–472 (1981).

The replacement of two hydrogen atoms in the 3-position of a compound of the formula II by methylidene substituted with a hydrocarbon or heterocyclic radical can be effected e.g. by an aldol condensation reaction of a compound of the formula II with an aldehyde XCHO, wherein X is a hydrocarbon or heterocyclic radical, in the presence of a base or an acid, according to "Methoden der Organischen Chemie" given in Houben-Weyl (4th Edition), Vol. VII/2b, pp. 1449–1529 (1976).

A number of compounds of the formula II as well as of the formulae III and IV are known, and others can be obtained analogously to known processes. Thus, compounds of the formula II, wherein Y is sulfur, sulfinyl or sulfonyl, can be produced for example by cyclisation of compounds of the formula IIa

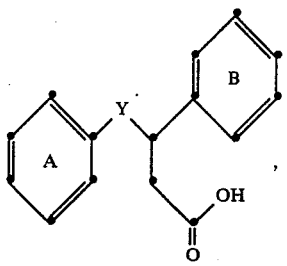 (IIa)

wherein Y is sulfur, sulfinyl or sulfonyl and A and B have the meanings defined above, with e.g. a phosphorous oxyhalide, preferably phosphorous oxychloride.

Compounds of the formula II wherein Y is oxygen can for example further be obtained by cyclisation of 2'-hydroxychalcones of the formula IIb

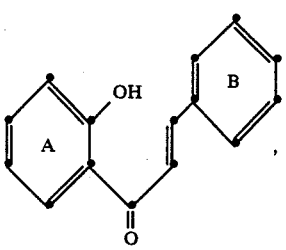 (IIb)

in which A and B have the meanings defined above according to J. Wiley (Ed.), The Chemistry of Chalcones and Related Compounds, pp. 96–97, N.Y. 1981.

Compounds of the formula II, wherein Y is sulfinyl and A and B have meaning as defined under formula I, can be produced e.g. by oxidation of a corresponding compound of the formula II, wherein Y is sulfur and A and B have the meanings defined under the formula I, in the usual manner. The oxidation to sulfinyl can be effected for example by inorganic peracids, such as peracids of mineral acids, for example periodic acid or persulfuric acid; organic peracids, such as percarboxylic or persulfonic acids, for example performic, peracetic or trifluoroperacetic acid, m-chloroperbenzoic acid or p-toluenepersulfonic acid; by mixtures consisting of hydrogen peroxide and acids, for example mixtures of hydrogen peroxide and acetic acid.

The oxidation is preferably carried out in the presence of suitable catalysts, for example acids, which are suitable as catalysts, such as optionally substituted carboxylic acids, for example acetic or trifluoroacetic acid, or oxides of transition metals, such as the oxides of the elements of the auxiliary group VII, for example vanadium, molybdenum or tungsten oxide.

Compounds of the formula II, wherein Y is sulfonyl and A and B have meaning as defined under formula I, can be obtained e.g. by oxidation of a corresponding compound of the formula II, wherein Y is sulfur or sulfinyl and A and B have the meanings defined under the formula I, for example with dinitrogentetroxide as a catalyst, in the presence of oxygen at low temperature, and using the same oxidation means as just described above for the oxidation to sulfinyl, but usually taking an excess of them.

On the contrary, compounds of the formula II, wherein Y is sulfinyl or sulfonyl, can be reduced to compounds of the formula II, wherein Y is sulfur. A suitable reduction means is for example catalytically activated hydrogen using nobel metals or their oxides as catalysts, such as palladium, platinum or rhodium or their oxides respectively, which are optionally distributed on a suitable carrier, such as charcoal or barium sulfate.

Furthermore, reducing metal cations, such as tin(II), lead(II), copper(I), manganese(II), titanium(II), vanadium(II), molybdenum (III) or tungsten(III) compounds; hydrogen halides, such as hydrogen chloride, bromide or iodide; hydrides, such as complex metal hydrides, for example lithium aluminium, sodium boro- or tributyltin hydride; phosphorous compounds, such as phosphorous halides, for example phosphorous trichloride or -tribromide, phosphorous pentachloride or -oxychloride; phosphines, such as triphenylphosphine; or phosphorous pentasulfide-pyridine; or sulfur compounds, such as mercaptanes, thioacids, thiophosphorous acids or dithiocarboxylic acids, dithionite or sulfur complexes, such as the iodine-pyridinesulfurdioxide complex, can be used as reducing agents.

It is also possible in essentially the same manner as described above for compounds of the formula II to convert compounds of the formula I, wherein Y is sulfur, sulfinyl or sulfonyl, and A, B and X have the meanings given under the formula I, into other compounds of the formula I, wherein Y is sulfinyl, sulfonyl or sulfur, provided that functional groups eventually present which are sensitive to the above-described oxidation and reduction methods, for example formyl, mercapto or amino, are protected by conventional protecting groups.

In the starting compounds of the formulae II, IIa, IIb, VI and VIa, as well as in compounds of the formula I to be converted into another compound of the formula I, functional groups present, especially formyl, carboxy, amino, hydroxy and mercapto groups, and also sulfo groups, are optionally protected by conventional protecting groups that are customary in preparative organic chemistry. Protected carboxy, amino, hydroxy, mercapto and sulfo groups are those that can be converted under mild conditions into free carboxy, amino, hydroxy, mercapto and sulfo groups without the molecular framework being destroyed or other undesired side reactions taking place.

The purpose of introducing protecting groups is to protect the functional groups from undesired reactions with reaction components and thus prevent them of being removed or converted into a derivative. On the other hand, reaction components can be consumed or bonded in an undesired manner by reaction with an unprotected functional group and are then no longer available for the actual reaction. The choice of protecting groups for a particular reaction depends on the nature of the functional group to be protected (carboxy group, amino group etc.), the structure and stability of the molecule of which the substituent is the functional group, and the reaction conditions.

Protecting groups that meet these conditions and their introduction and removal are known and are described, for example, in J. F. W. McOmie, "Protective Groups in Organic Chemistry", Plenum Press, London, N.Y. 1973, T. W. Greene, "Protective Groups in Organic Synthesis", Wiley, N.Y. 1981, and also in "The Peptides", Vol. I, Schroeder and Luebke, Academic Press, London, N.Y. 1965, as well as in Houben-Weyl, "Methoden der Organischen Chemie", Vol. 15/1, Georg Thieme Verlag, Stuttgart, 1974.

Compounds of the formula I obtained can be converted into other compounds of the formula I in a manner known per se.

For example, compounds of the formula I in which X is mono- or disubstituted amino can be obtained from corresponding compounds in which X is unsubstituted or substituted amino e.g. by reaction with primary or secondary amines, especially lower alkylamines, di-lower alkylamines or lower alkyleneamines, such as piperidine, morpholine or thiomorpholine, in benzene according to Bull. Chem. Soc. Jap. 52, pp. 1735-1737 (1979); preferably in a sealed tube and at a temperature of 25°-225° C. A further process variant for the manufacture of compounds of the formula I in which X is substituted amino consists of the alkylation of compounds of the formula I in which X is unsubstituted amino by alkylation means, for example by reaction with an alkyltosylate, such as methyltosylate, in the presence of a base, for example sodium hydride, according to Bull. Chem. Soc. Jap. 52, pp. 1735-1737 (1979), or by reaction with a di-lower-alkylsulfate, for example dimethyl sulfate or diethyl sulfate according to Houben-Weyl, 4th Edition, Vol. XI/1, pp. 34-53, or by reaction with an alkyl halide, for example ethyl bromide or methyl iodide according to Houben-Weyl, 4th Edition, Vol. XI/1, pp. 205-207.

Compounds of the formula I in which X is unsubstituted amino can be converted into compounds of formula I wherein X is acylamino e.g. by reaction with free carboxylic acids or reactive derivates thereof. The reaction with free carboxylic acids is performed advantageously in the presence of an acid catalyst splitting off water, such as a protonic acid, for example hydrochloric or hydrobromic acid, sulfuric, phosphoric or boric acid, benzenesulfonic or toluenesulfonic acid, or a Lewis acid, for example borontrifluoride etherate, preferably, in an excess of the employed amino compound of the formula I and/or in an inert solvent, for example in a hydrocarbon of the benzene series, such as benzene or toluene, in a halogenated hydrocarbon, such as chloroform, methylene chloride or chlorobenzene, or in an ether-like solvent, such as tetrahydrofuran, if necessary with removal by distillation, for example azeotropic distillation, of the water released during the reaction. The reactions can also be performed in the presence of other water-binding condensation agents, for example carbodiimides substituted by hydrocarbon radicals, such as N,N'-diethyl-, N,N'-dicyclohexyl- or N-ethyl-N'-(3-dimethylaminopropyl)-carbodiimide, in inert organic solvents, for example in the aforementioned. Reactive derivatives of carboxylic acids, such as acid halides, for example acid chlorides, and mixed anhydrides, for example with acetic acid, are reacted for example in the presence of acid-binding agents, for example organic, especially tertiary, nitrogen bases, for example triethylamine, N,N-diisopropyl-N-ethylamine or pyridine [J. Org. Chem. 40, pp. 526-527 (1975)[, or in the presence of inorganic bases, for example alkali metal- or alkaline-earth metal-hydroxides or -carbonates, such as sodium, potassium or calcium hydroxide or -carbonate, in inert organic solvents, for example in the above-mentioned and if necessary with heating. In principle, the acid-binding agent can also be an excess of the amino compound of the formula I to be reacted.

Furthermore, compounds of the formula I in which X is unsubstituted or substituted amino can be converted into compounds of formula I in which X is hydroxy e.g. by heating in the presence of a base, such as potassium carbonate, or in the presence of hydrohalic acid, such as hydrochloric acid.

Compounds of the formula I in which X is disubstituted amino can be converted into compounds of formula I in which X is an unsubstituted or substituted hydrocarbon radical, or heterocyclic radical e.g. by reaction with an alkyllithium reagent, such as n-butyllithium, in the presence of an ether, for example tetrahydrofuran, as a solvent, preferably under an inert gas atmosphere, such as nitrogen, according to J. Org. Chem. 43, pp. 4248–4250 (1978).

A further process variant consists of the use of an alkylmagnesium halide, such as methyulmagnesium iodide, instead of the alkyllithium reagent according to Chem. Rev. 66, pp. 171–172 (1966).

Compounds of the formula I in which X is unsubstituted or substituted amino can be converted into compounds of the formula I in which X is etherified mercapto e.g. by reaction with an alkyl- or arylmercaptane in the presence of a base, such as potassium carbonate, in an aprotic solvent, as for example dimethylformamide, or protic solvent, such as ethanol.

Compounds of the formula I, wherein X is di-lower-alkylamino, can be converted into compounds of formula I, in which X is esterified mercapto, e.g. by reacting them with a thiol-lower-alkanecarboxylic acid, e.g. thiolacetic acid. Resulting compounds of the formula I, wherein X is esterified mercapto can be hydrolysed, preferably with a base, e.g. sodium hydroxide, to other compounds of the formula I, wherein X is mercapto.

Compounds of the formula I, wherein X is mercapto, can be converted into other compounds of the formula I, wherein X is sulfo, by oxidation e.g. with potassium peroxodisulfate according to U.S. Pat. No. 2,727,057.

Resulting compounds of the formula I, wherein X is sulfo, can be converted into compounds of the formula I, wherein X is functionally modified sulfo, in a manner known per se, e.g. analogously to the conversions of carboxy into functionally modified carboxyl described below.

Compounds of formula I in which X is a quaternary ammonium salt can be converted into compounds of formula I in which X is nitro e.g. by reaction with sodium nitrite according to Chem. Rev. 66, pp. 172–173 (1966).

Furthermore, compounds of the formula I in which X is cyano can be obtained e.g. from compounds of formula I in which X is a quaternary ammonium salt by reaction with an alkali cyanide, for example sodium cyanide, according to Chem. Rev. 66, p. 173 (1966).

Compounds of the formula I in which X is free or metallised hydroxy can be converted into a compound of the formula I in which X is an ether group defined above e.g. by reaction with a compound of formula IVa $$A_1-R \qquad (IVa),$$

wherein $A_1$ is a free, metallised, or reactively esterified hydroxyl group, and R together with an oxygen atom attached thereto corresponds to one of the above-defined ether groups, or $A_1$-R is a compound introducing the ether radical R.

If $A_1$-R is a compound introducing the radical R, it can be e.g. a corresponding diazo compound, an acetal corresponding to the alcohol R OH, or a corresponding ortho ester, a corresponding oxonium, carbenium or halonium salt or a corresponding triazene compound. The reaction is performed preferably in the presence of proton donors, that is to say, by means of acid catalysis.

The proton donors used are in paricular strong inorganic acids or organic sulfonic acids, for example mineral acids, such as hydrohalic acids, for example hydrochloric acid, also sulfuric acid, or for example p-toluenesulfonic acid, but also Lewis acids, such as halides of boron, aluminium or zinc, for example boron trifluoride, aluminium chloride or zinc chloride. Etherification is preferably performed without an addition of solvent in the corresponding alcoholic solution, that is, in an alcohol of the formula ROH, provided this is in the liquid state at the applied temperature.

If X is a hydroxyl group which is metallised, preferably metallised by an alkali metal atom, for example ONa, $A_1$ is present as a reactive esterified hydroxyl group. A reactive esterified hydroxyl group $A_1$ is preferably a hydroxyl group esterified by a strong mineral or sulfonic acid, such as a hydrohalic acid, sulfuric acid, lower-alkanesulfonic acid or benzenesulfonic acid, for example hydrochloric, hydrobromic, methanesulfonic, trifluoromethanesulfonic, benzenesulfonic or p-toluenesulfonic acid. Such esters are, inter alia: lower alkyl halides, di-lower-alkyl sulfates, such as dimethyl sulfate, also fluorosulfonic acid ester, such as lower alkyl ester, for example fluorosulfonic acid-methyl ester, or unsubstituted or halogen-substituted methanesulfonic acid-lower-alkyl ester, for example trifluoromethanesulfonic acid-methyl ester. The hydroxyl group of the starting material of the formula IVa can however also be esterified for example by a lower alkanecarboxylic acid, such as acetic acid or propionic acid. Etherification can be performed in the presence of basic condensation agents which bind the formed acids. Such agents are carbonates or hydrogen carbonates of alkaline-earth metals or alkali metals, for example calcium or sodium carbonates or -hydrogen carbonates, or tertiary amines, for example tri-lower-alkylamines, pyridines or lower-alkylated pyridines. If the one starting material is used in the form of the metallised compound (for example X=ONa), the reaction preferably is performed under neutral reaction conditions. Finally, when $A_1$ is a hydroxyl group esterified by a lower alkanecarboxylic acid, for example a hydroxyl group esterified by acetic acid, the reaction with a corresponding hydroxy compound of formula I is advantageously performed in an acid medium, preferably in the presence of a mineral acid, for example a hydrohalic acid, such as hydrochloric acid. The reactions are performed, if necessary, with the addition of an inert solvent, such as an optionally halogenated (such as chlorinated) aliphatic, cycloaliphatic or aromatic hydrocarbon, for example methylene chloride, of an ether, such as dioxane or tetrahydrofuran, or of a mixture of these solvents.

The above-described etherification reaction can be considerably accelerated by phase-transfer catalysis [cp. Dehmlow, Angewandte Chemie, Vol. 5, p. 187 (1974)]. Suitable phase-transfer catalysts are e.g. quaternary phosphonium salts and particularly quaternary ammonium salts, such as unsubstituted or substituted tetraalkylammonium halides, for example tetrabutylammonium chloride, -bromide or -iodide, or benzyltriethylammonium chloride, used in catalytic or up to equimolar amounts. The organic phase used can be any solvent immiscible with water, for example one of the optionally halogenated (such as chlorinated), lower aliphatic, cycloaliphatic or aromatic hydrocarbons, such as tri- or tetrachloroethylene, tetrachloroethane, carbon tetrachloride, chlorobenzene, toluene or xylene. Alkali metal carbonates or -hydrogen carbonates suitable as condensation agents are for example: potassium or sodium carbonate or -hydrogen carbonate, alkali metal phosphates, for example potassium phosphate, and alkali metal hydroxides, for example sodium hydroxide.

Compounds of the formula I wherein X is a free hydroxyl group can be etherified, as already stated above, also by reaction with corresponding diazo compounds. Such compounds are for example: diazo-lower-alkanes, such as diazomethane, diazoethane or diazo-n-butane, but also phenyldiazo-lower-alkanes, for example phenyl-diazomethane. These reagents are applied in the presence of a suitable inert solvent, such as an aliphatic, cycloaliphatic or aromatic hydrocarbon, such as hexane, cyclohexane, benzene or toluene, or in the presence of a halogenated aliphatic hydrocarbon, for example methylene chloride, or an ether, such as di-lower-alkyl ether, for example diethyl ether, or in the presence of a cyclic ether, for example tetrahydrofuran or dioxane, or a solvent mixture, and, depending on the diazo reagent, with cooling, at room temperature or with slight heating, also, if necessary, in a closed vessel and/or under an inert gas, for example in a nitrogen atmosphere.

Further etherifying agents are suitable acetal compounds, for example gem-di-lower-alkoxy-lower alkanes, such as 2,2-dimethoxy-propane, which are used in the presence of strong organic sulfonic acids, such as p-toluenesulfonic acid, and of a suitable solvent, such as a di-lower-alkyl- or lower-alkylenesulfoxide, for example dimethyl sulfoxide; or suitable ortho esters, for example orthoformic acid-tri-lower-alkyl esters, for example orthoformic acid-triethyl esters, which are used in the presence of a strong mineral acid, for example sulfuric acid, or a strong organic sulfonic acid, such as p-toluene-sulfonic acid, and a suitable solvent, such as an ether, for example dioxane.

Further etherifying agents are corresponding tri-substituted oxonium salts (so-called Meerwein salts), or disubstituted carbenium or halonium salts, wherein the substituents are the ethrifying radicals R, for example tri-lower-alkyloxonium salts, and di-lower-alkoxy-carbenium or di-lower-alkylhalonium salts, especially the corresponding salts with complex, fluorine-containing acids, such as the corresponding tetrafluoroborates, hexafluorophosphates, hexafluoroantimonates or hexachloroantimonates. Such reagents are for example: trimethyloxonium- or triethyloxonium-hexafluoroantimonate, -hexachloroantimonate, -hexafluorophosphate or -tetrafluoroborate, dimethoxycarbeniumhexafluorophosphate or dimethylbromoniumhexafluoroantimonate. These etherifying agents are used preferably in an inert solvent, such as in an ether or a halogenated hydrocarbon, for example diethyl ether, tetrahydrofuran or methylene chloride, or in a mixture thereof, if necessary in the presence of a base, such as an organic base, for example a preferably sterically hindered, tri-lower-alkylamine, for example N,N-diisopropyl-N-ethylamine.

Further etherifying agents are e.g. corresponding 1-substituted 3-aryltriazene compounds wherein the substituent is the etherifying radical R, and aryl is preferably unsubstituted or substituted phenyl, for example lower alkylphenyl, such as 4-methylphenyl. Such triazene compounds are 3-aryl-1-lower-alkyltriazenes, for example 3-(4-methylphenyl)-1-methyl-triazene, 3-(4-methylphenyl)-1-ethyl-triazene or 3-(4-methylphenyl)-1-isopropyl-triazene. These reagents are used usually in the presence of inert solvents, such as optionally halogenated hydrocarbons or ethers, for example benzene, or solvent mixtures.

The conversion of a compound of the formula I, wherein X is hydroxy, into a compound of the formula I, wherein X is halogen, is usually performed by treatment with a halogenating, especially chlorinating, agent. Such agents are for example: thionyl chloride, thionyl bromide, phosphorus tribromide, phosphorus oxybromide or -chloride or phosphorus pentachloride, which are usually used in the presence of an inert solvent or diluent, for example tetrahydrofuran, dioxane, methylene chloride or dimethyl sulfoxide.

As a process variant, starting again with a compound of the formula I, wherein X is hydroxy, it is also possible first to produce a compound of formula I, wherein X is hydroxy esterified e.g. by a lower-alkyl- or arylsulfonic acid, such as me sylate or tosylate, by reaction with e.g. lower-alkylsulfonyl chloride or p-toluenesulfonyl chloride, and then to treat the latter with an alkalimetal halide, e.g. potassium fluoride, cesium fluoride or sodium chloride, preferably in the presence of a crown ether, yielding a compound of the formula I, wherein X is halogen.

Compounds of the general formula I, in which X is an acyloxy group, can be obtained e.g. by converting a compound of formula I, in which X is a free hydroxyl group, with an acylating agent introducing the desired acyl radical of an organic carboxylic acid, into an acyloxy group. Such agents are for example corresponding carboxylic acids or reactive derivatives thereof, such as anhydrides or acid halides, for example acid chlorides or acid bromides. The reactions can be performed optionally in the presence of condensation agents, in the case of free carboxylic acids, for example, in the presence of carbodiimide compounds, such as dicyclohexylcarbodiimide, or carbonyl compounds, such as diimidazolylcarbonyl. With the use of acid derivatives, for example acid halides, the reactions are performed advantageously in the presence of a basic agent, for example a tri-lower-alkylamine, such as triethylamine, or in the presence of a heterocyclic base, for example pyridine.

Compounds of the formula I wherein X is lower alkoxy can be converted into other compounds of the formula I wherein X is another lower alkoxy group, OR, e.g. by treatment with a lower alkanol of the formula ROH, optionally in the presence of an acid.

Compounds of the formula I wherein X is hydroxy can be converted into compounds of the formula I wherein X is unsubstituted or substituted amino e.g. by reaction with anhydrous ammonia or the corresponding amine respectively e.g. in a lower alkanol, such as ethanol, according to Bull. Chem. Soc. Japan 52, 1735 (1979).

Compounds of the formula I wherein X is etherified mercapto can be obtained from compounds of the formula I wherein X is hydroxy or esterified hydroxy, especially hydroxy esterified by lower-alkyl or arylsulfonic acids, such as mesylate or tosylate, e.g. by reaction with a lower-alkyl- or arylmercaptane according to J. Org. Chem. 27,1615, 1620 (1962); Tetrahedron Letters 1979, 1015; J. Amer. Chem. Soc. 93, 1027 (1971); and J. Med. Chem. 24, 468 (1981).

Compounds of the formula I wherein X is halogen can be converted into compounds of the formula I wherein X is unsubstituted or substituted amino, quaternary ammonium salt, hydrazino, free or etherified hydroxy or etherified mercapto e.g. by reaction with the corresponding nucleophiles as there are ammonia, mono- or disubstituted amine, trisubstituted amine, aqueous hydrazine, an alkaline hydroxide, such as potassium hydroxide or a metallised hydroxy or mercapto compound, such as sodium ethoxide or phenoxide, or sodium methylmercaptide according to Chem. Rev. 66, pp. 183, 186 (1966).

Compounds of the formula I wherein X is halogen can be converted into compounds of formula I wherein X is an alkyl or aryl group e.g. by reaction with an alkyl- or arylmagnesiumhalide, such as ethylmagnesiumbromide or phenylmagnesiumbromide according to Chem. Rev. 66, pp. 182-183 (1966).

Compounds of the formula I wherein X is cyano can be obtained from compounds of formula I wherein X is halogen e.g. by reaction with cyanides, preferably alkaline metal cyanides, such as sodium cyanide, according to Chem. Rev. 66, pp. 182-183 (1966).

Compounds of the formula I wherein X is cyano can be hydrolysed to corresponding compounds of the formula I wherein X is carbamoyl, or directly to compounds of the formula I wherein X is carboxy in customary manner, for example in the presence of concentrated aqueous mineral acids or alkali metal hydroxides.

Compounds of the formula I wherein X is cyano can also be alcoholysed to form corresponding compounds of the formula I having esterified carboxy groups as X in customary manner, for example by the addition of alcohols in the presence of an anhydrous acid, such as hydrogen chloride, and subsequent hydrolysis of the resulting imido ester.

Compounds of the formula I wherein X is carboxy can be converted to compounds of the formula I wherein X is esterified carboxyl in customary manner, for example by reacting with a corresponding alcohol, advantageously in the presence of an acid, such as a mineral acid, for example sulfuric acid or hydrochloric acid, or in the presence of a water-binding agent, such as dicyclohexylcarbodiimide, or by reacting with a corresponding diazo compound, for example diazomethane. Esterification can also be carried out e.g. by reacting a salt, preferably an alkali metal salt, of the acid with a reactive esterified alcohol, for example a corresponding halide, such as chloride.

Compounds of the formula I wherein X is carboxy can be converted to compounds of the formula I wherein X is amidated carboxyl in customary manner, for example by reacting with ammonia or with a primary or secondary amine, advantageously in the presence of a water-binding agent, such as dicyclohexylcarbodiimide, or by converting the carboxy group into a halocarbonyl group, for example a chlorocarbonyl group, and then reacting with ammonia or a primary or secondary amine.

Compounds of the formula I that contain as X an esterified carboxyl group, can be converted to another compound of the formula I wherein X is carboxy in customary manner, for example by hydrolysis, preferably in the presence of strong bases, such as an alkali metal hydroxide, for example sodium or potassium hydroxide, or strong acids, for example a strong mineral acid, such as a hydrohalic acid, for example hydrochloric acid, or sulfuric acid.

Compounds of the formula I having an esterified carboxyl group as X, can be converted to corresponding compounds of the formula I wherein X is a carbamoyl group in customary manner, for example by ammonolysis or aminolysis with ammonia or a primary or secondary amine.

Compounds of the formula I having a carbamoyl group as X can be dehydrated to form corresponding compounds of the formula I wherein X is cyano in customary manner, for example by the action of dehydrating agents, such as phosphorous pentoxide, phosphorous oxychloride or trifluoroacetic acid anhydride, preferably at elevated temperatures.

Compounds of the formula I having an esterified carboxyl group as X can be converted to compounds of the formula I wherein X is cyano in customary manner, for example by the action of an organic aluminium amide compound, such as a di-lower alkylaluminium amide compound, for example diethylaluminium amide.

Compounds of the formula I in which X is unsubstituted or monosubstituted amino can be also obtained by sulfur extrusion of a compound of the formula VI

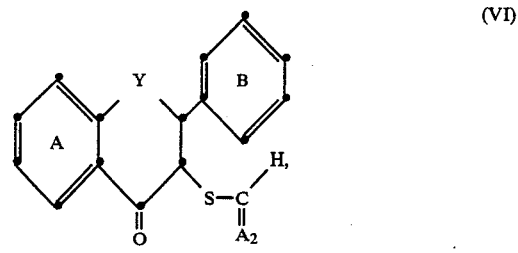

in which $A_2$ is unsubstituted or substituted imino, and A, B and Y have meaning as defined under formula I, using e.g. a strong base, such as sodium methoxide, according to Synthesis, 1976, pp. 535-537.

Compounds of formula I in which X is hydroxy can be also obtained by sulfur extrusion of a compound of the formula VI, in which $A_2$ is oxygen and A, B and Y have the meanings defined under the formula I, using e.g. triphenylphosphine according to Helv. Chim. Acta, Vol. 54, pp. 710-734 (1971).

The starting materials of the formula VI can be synthesized in a manner known per se. For example, compounds of the formula VI wherein $A_2$ is unsubstituted or substituted imino can be prepared by reaction of an α-bromoketone of the formula VIa

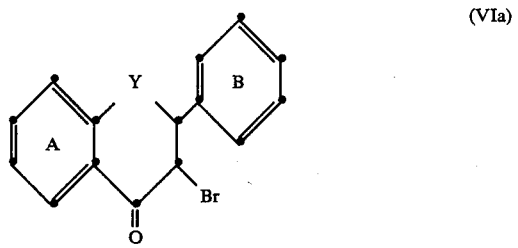

with a secondary thioamide, $R_3HN\text{-}CH=S$, wherein $R_3$ is alkyl or aryl, and subsequent treatment with a base, for example pyridine, to yield the free imino compound according to Synthesis 1976, pp. 535-537.

Compounds of formula VI wherein $A_2$ is oxygen can be obtained e.g. by reaction of a compound of the formula VIa with thiolformic acid, HCOSH, according to Helv. Chim. Acta 54, pp. 710-734 (1971).

Furthermore, it is possible within the scope of the definition of the compounds of the formula I to convert compounds obtained in customary manner into other compounds of the formula I by modifying, introducing or splitting off suitable substituents within the radical X and the rings A and B.

Free carboxy groups can be esterified in essentially the same manner as described above for compounds of the formula I having a carboxy grous as X.

Free carboxy groups can be amidated in essentially the same manner as described above for compounds of the formula I having a carboxy group as X.

In compounds that contain an esterified carboxyl group, the latter can be converted into a free carboxy group in essentially the same manner as described above for compounds of the formula wherein X is esterified carboxyl.

In compounds having an esterified carboxyl group as substituent, the latter can be converted into the corresponding carbamoyl group in customary manner, for example by ammonolysis or aminolysis with ammonia or a primary or secondary amine.

Compounds having a carbamoyl group as substituent can be dehydrated to form the corresponding cyano compounds in essentially the same manner as described above for compounds of the formula I having a carbamoyl group as X.

In compounds having an esterified carboxyl group as substituent, the esterified carboxyl group can be converted into a cyano group in customary manner, for example by the action of an organic aluminium amide compound, such as a di-lower alkylaluminium amide compound, for example diethylaluminium amide.

Compounds containing a cyano substituent can be hydrolysed to the corresponding carbamoyl compounds or directly to the carboxy compounds in customary manner, for example in the presence of concentrated aqueous mineral acids or alkali metal hydroxides.

Compounds having a cyano group as substituent can be alcoholysed to form corresponding compounds having esterified carboxyl groups in essentially the same manner as described above for compounds of the formula I wherein X is cyano.

Compounds of the formula I containing a primary or secondary amino group as substituent can be converted into compounds of the formula I which contain a tertiary amino group by introducing a substituent, for example an optionally substituted lower alkyl group, such as methyl or benzyl, in customary manner, for example using a corresponding reactive esterified alcohol, such as a corresponding halide, for example chloride or bromide, or a diazoalkane, for example diazomethane.

Compounds that carry as substituent a lower alkylthio group, for example a methylthio group, can be converted into the sulfur-free compounds by treating with suitable desulfurating agents, for example Raney nickel, in a suitable solvent, for example dioxane.

In compounds of the formula I which carry a phenolic hydroxy group as substituent this may be etherified in customary manner. The reaction to form the corresponding ethers is carried out, for example, in the presence of bases, such as alkali metal hydroxides or carbonates, for example sodium hydroxide or potassium carbonate, by means of di-lower-alkyl-sulfates or lower alkyl halides or in the presence of a dehydrating agent, for example dicyclohexylcarbodiimide, by means of lower alkanols.

In compounds of the formula I in which an aliphatically or cycloaliphatically bonded hydroxy or mercapto group is present as substituent, this group may be etherified in customary manner. Suitable etherifying agents are e.g. diazo compounds, such as unsubstituted or substituted diazo-lower alkanes, for example diazomethane. Further suitable etherifying agents are esters of corresponding alcohols, especially those with strong inorganic or organic acids, such as mineral acids, e.g. hydrohalic acids, such as hydrochloric acid, and also sulfuric acid, or strong sulfonic acids, such as lower alkanesulfonic acids which are unsubstituted or substituted e.g. by lower alkyl, such as methyl, for example methanesulfonic acid, trifluoromethanesulfonic acid or p-toluenesulfonic acid. Such esters are for example lower alkyl halides, for example methyl iodide, or sulfates, such as dimethyl sulfate.

Compounds of the formula I containing an esterified hydroxy and/or mercapto group as substituent can be obtained e.g. by treating a compound of formula I, in which a hydroxy and/or mercapto group is present as substituent, with an acylating agent introducing the desired acyl radical. Such agents are, for example, optionally substituted lower alkanecaboxylic or lower alkanesulfonic acids, optionally substituted benzoic or phenylsulfonic acids or reactive derivatives thereof, such as anhydrides or acid halides, for example acid chlorides, e.g. acetylchloride, methylsulfonyl chloride, benzoyl chloride or p-tolylsulfonyl chloride, or hydrohalic acids, especially in the form of reactive esters, for example thionylchloride and phosphorous tribromide.

Conversely, compounds of the formula I containing an esterified hydroxy and/or mercapto group as sustituent can be converted into corresponding compounds of the formula I which carry a hydroxy and/or mercapto group as substituent. The conversion to hydroxy and/or mercapto is carried out, for example, by alcoholysis with a lower alkanol, vor example methanol or ethanol, or preferably by hydrolysis, such as base-catalysed hydrolysis, for example in the presence of sodium hydroxide.

Lower alkoxy and phenoxy groups as well as lower alkylthio and phenylthio groups can be converted to free hydroxy and free mercapto groups by mineral acids, e.g. hydrohalic acids, such as hydroiodic acid, or Lewis acids, for example aluminium trichloride.

As in the manufacturing processes, when carrying out the additional steps, care must be taken that undesired side reactions which may result in the conversion of additional groupings do not occur.

The reactions described above may be carried out simultaneously or in succession, as desired, and also in any sequence. If necessary, they are carried out in the presence of diluents, condensation agents and/or catalytically active agents, at reduced or elevated temperature, in a closed vessel under pressure and/or in an inert gas atmosphere.

Acid addition salts of compounds of the formula I with salt-forming groups are obtained in customary manner, for example by treating with an acid or a suitable anion exchanger. The resulting salts can be converted into the free compounds in a manner known per se, for example by treating with a suitable basic agent, for example a metal hydroxide, ammonia or a hydroxyl ion exchanger. On the other hand, compounds having an acidic group, e.g. a carboxy or a phenolic hydroxy group, can be converted into an alkali metal salt in a manner known per se by treating, for example, with an alkali metal hydroxide. The free compounds can be obtained by treating with an acid.

Salts of compounds of the formula I are especially pharmaceutically acceptable non-toxic salts, such as those of compounds of the formula I with acidic groups, for example with a free carboxyl or sulfo group. Such salts are especially metal or ammonium salts, such as alkali metal or alkaline earth metal salts, for example sodium, potassium, magnesium or calcium salts, as well as ammonium salts, which are formed with ammonia or suitable organic amines. There come into consideration for the salt formation especially aliphatic, cycloaliphatic, cycloaliphatic-aliphatic or araliphatic primary, secondary or tertiary mono-, di- or poly-amines, as well as heterocyclic bases, such as lower alkylamines, for example di- or tri-ethylamine, hydroxy-lower alkylamines, for example 2-hydroxyethylamine, bis-(2-hydroxyethyl)-amine or tris-(2-hydroxyethyl)-amine, basic aliphatic esters or carboxylic acids, for example 4-aminobenzoic acid, 2-diethylaminoethyl ester, lower alkyleneamines, for example 1-ethylpiperidine, cycloalkylamines, for example dicyclohexylamine, or benzylamines, for example N,N'-dibenzylethylenediamine.

Compounds of the formula I having a basic group may form acid addition salts, for example with inorganic acids, such as hydrochloric acid, sulfuric acid or phosphoric acid, or with suitable organic carboxylic or sulfonic acids, for example acetic acid, succinic acid, fumaric acid, tartaric acid, methanesulfonic acid and p-toluenesulfonic acid. In the presence of several acidic or basic groups, mono- or poly-salts may be formed. Compounds of the formula I having an acidic group, for example a free carboxy group, and a basic group, for example an amino group, may also be present in the form of inner salts, i.e. in zwitterionic form, or a part of the molecule may be present in the form of an inner salt and another part in the form of a normal salt.

The pharmaceutically acceptable salts mentioned hereinbefore are preferred. For isolation or purification it is also possible to use other salts than the therapeutically acceptable salts, for example the picrates. Owing to the close relationships between the novel compounds in free form and in the form of their salts, hereinbefore and hereinafter there shall optionally be understood by free compounds and salts, where appropriate with regard to meaning and purpose, also the corresponding salts and free compounds, respectively.

The compounds of formula I, including their salts, can also be obtained in the form of their hydrates or can include the solvent used for their crystallisation.

The compounds of the formula I have at least one asymmetric center at the carbon atom 2. Therefore they can be found as R- or S-enantiomers as well as a racemate. The present invention is intended to include all these forms, also those further stereoisomers, and mixtures of at least two stereoisomers, for example a diastereomeric mixture or enantiomeric mixture, such as a racemate, which are possible if one or more other asymmetric centers are present within the molecule.

Starting materials and end products that are isomeric mixtures can be separated into the individual isomers by methods known per se, for example by fractional distillation, crystallisation and/or chromatography. Racemic products can be separated into the optical antipodes, for example by chromatography and/or separation of their diastereoisomeric salts, for example by fractional crystallisation of the d- or l-camphor-sulfonates, -mandelates, -tartrates or -dibenzoyltartrates.

The invention relates also to modifications of the present process, according to which an intermediate obtainable at any stage of the process is used as starting material and the remaining process steps are carried out, or the process is discontinued at any stage, or according to which a starting material is formed under the reaction conditions, or in which a starting material is used in the form of a salt or a reactive derivative. The invention also comprises novel intermediates therefrom.

In the process of the present invention the starting materials used are preferably those which result in the compounds described at the beginning as being especially valuable.

The starting materials used in the process for the manufacture of the compounds of the present invention are known or, if they are novel, they can be manufactured by methods known per se. The invention relates also to novel starting materials.

The invention further relates to the use of the compounds of formula I as pharmacologically active compounds or for the manufacture of pharmaceutical preparations.

The pharmaceutical preparations according to the invention contain at least one compound of the general formula I or a salt thereof as the active substance together with a customary pharmaceutical carrier. The type of carrier depends largely on the field of use. The pharmaceutical compositions according to the invention which contain, as active substances, compounds of the formula I can be administered enterally, such as orally or rectally, parenterally, e.g. subcutaneously, intramuscularly or intravenously, or by inhalation.

For oral treatment, especially solid dosage unit forms, such as tablets, dragees and capsules are considered, which preferably contain between 10 and 90% of an active substance of the general formula I or a salt in order to allow administration to warm-blooded animals of daily doses of from 0.1 to 100 mg/kg, especially from 1 to 50 mg/kg. The daily dose depends on age and individual condition and also on the mode of administration. For the manufacture of tablets and dragee cores, the compounds of the general formula I are combined with solid, pulverulent carriers, such as lactose, saccharose, sorbitol, maize starch, potato starch or amylopectin, cellulose derivatives or gelatine, preferably with the addition of lubricants, such as magnesium or calcium stearate, or polyethylene glycois of a suitable molecular weight. Dragee cores are subsequently coated, for example with concentrated sugar solutions which may contain, in addition, gum arabic, talc and/or titanium dioxide, or with a lacquer dissolved in readily volatile organic solvents or solvent mixtures. Colouring substances can be added to these coatings, for example for indicating different doses of active substance. Soft gelatine capsules and other closed capsules consist, for example, of a mixture of gelatine and glycerin and may contain, for example, mixtures of a compound of the formula I and polyethylene glycol. Dry-filled capsules contain, for example, granules of an active substance with solid, pulverulent carriers, such as, for example, lactose, saccharose, sorbitol, mannitol; starches, such as potato starch, maize starch or amylopectin, cellulose derivatives and gelatine and also magnesium stearate or stearic acid.

Unit dosage forms that come into consideration for rectal administration are, for example, suppositories which consist of a combination of an active substance with a suppository base based on natural or synthetic triglycerides (for example cocoa butter), polyethylene glycols or suitable higher fatty alcohols, and gelatine rectal capsules which contain a combination of the active substance with polyethylene glycols.

Ampoule solutions for parenteral administration, especially for intramuscular or intravenous administration, contain a compound of the formula I or a salt thereof in a concentration of preferably 0.5 to 5% as an aqueous dispersion prepared with the aid of customary solubilisers and/or emulsifiers, and, optionally, stabilisers, or preferably as an aqueous solution of a pharmaceutically acceptable water-soluble salt of a compound of the general formula I.

For inhalation the active compound may be presented in association with volatile excipients, as a cream, lotion, paste or ointment or as a finely divided dry powder or in solution for inhalation through a nasal spray, atomiser or insufflator.

Inhalation preparations for the treatment of the respiratory tract by nasal, buccal or intrapulmonary administration are e.g. aerosols or sprays that can disperse the pharmacological active ingredient in the form of a powder or in the form of drops of a solution or suspension. Preparations having powder-dispersing properties generally contain, apart from the active ingredient, a liquid propellant gas having a boiling point of below room temperature and, if desired, carriers, such as liquid or solid, non-ionic or anionic surface-active agents and/or solid diluents. Preparations in which the pharmacological active ingredient is in solution, contain, in addition, a suitable propellant, and also, if necessary, an additional solvent and/or a stabiliser. Instead of the propellant gas, it is also possible to use compressed air, and this can be produced as required by means of a suitable compression and release device.

The concentration of the active substance for liquids that are to be taken orally, such as syrups or elixirs, is so selected that a single dose can easily be measured, for example as the contents of a teaspoon or a measuring spoon of, for example, 5 ml, or also as a multiple of that volume.

The following Examples (a) to (c) are intended to illustrate the manufacture of some typical forms of administration, but do not in any way represent the only embodiments of those forms of administration.

(a) 250 g of active substance are mixed with 550 g of lactose and 292 g of potato starch, and the mixture is moistened with an alcoholic solution of 8 g of gelatine and granulated by being passed through a sieve. After drying, 60 g of talc, 10 g of magnesium stearate and 20 g of colloidal silica are added and the mixture is pressed to form 10,000 tablets each weighing 119 mg and each containing 25 mg of active substance, which may, if desired, be provided with dividing notches of a finer adjustment of the dosage.

(b) A granulate is prepared from 100 g of active substance, 379 g of lactose and the alcoholic solution of 6 g of gelatine, which, after being dried, is mixed with 10 g of colloidal silica, 40 g of talc, 60 g of potato starch and 5 g of magnesium stearate and pressed to form 10,000 dragee cores. These are subsequently coated with a concentrated syrup consisting of 533.5 g of cryst. saccharose, 20 g of shellac, 75 g of gum arabic, 250 g of talc, 20 g of colloidal silica and 1.5 g of colouring substance, and dried. The resulting dragees each weight 150 mg and each contain 10 mg of active substance.

(c) 25 g of active substance and 1975 g of finely ground suppository base (for example, cocoa butter) are thoroughly mixed and then melted. 1000 suppositories of 2 g are cast from the melt which has been kept homogenous by stirring. They each contain 25 mg of active substance.

The following Examples serve to illustrate the invention but are not intended to limit the scope thereof in any way. Temperatures are given in degrees Centigrade. Unless defined otherwise, the evaporation of solvents is carried out under reduced pressure, for example between approximately 0.1 and 20 mbar.

EXAMPLE 1

A solution of 23 g thioflavanone in 230 ml dimethylformamide is stirred at 100° C. under nitrogen. To this solution, 82 ml N,N-dimethylformamide diethylacetal is added and stirring is maintained one hour. The reaction mixture is then evaporated to dryness under vacuum and the residual solid is purified by column chromatography. The best fractions are recrystallised in a mixture of toluene and hexane and 3-N,N-dimethylaminomethylidene-thioflavanone is obtained as yellow crystals; m.p. 210°–211° C.

EXAMPLE 2

As in Example 1, but using 1 g 5-hydroxy-flavanone, 10 ml dimethylformamide and 3.6 ml N,N-dimethylformamide diethylacetal. 5-hydroxy-3-N,N-dimethylaminomethylidene-flavanone is obtained as yellow crystals after recrystallisation in a mixture of hexane and ethyl acetate; m.p. 179°–180° C.

EXAMPLE 3

A mixture of 25.4 g 6-methyl-thioflavanone, and 75 ml N,N-dimethylformamide diethylacetal is heated and stirred at 80° C. under nitrogen. A slow stream of nitrogen is bubbled through the reaction mixture and stirring is maintained eight hours.

At that time, 20 ml of distillate has been collected. The remaining N,N-dimethylformamide diethylacetal is distilled off in a high vacuum. The residue is taken up in 100 ml boiling toluene, the hot solution treated with charcoal, filtered and cooled. Yellow crystalline 3-N,N-dimethylaminomethylidene-6-methyl-thioflavanone is collected, washed with hexane and dried; m.p. 191°–193° C.

EXAMPLE 4

As in Example 3 but using 5 g 6-fluoro-flavanone, 5 ml dimethylformamide and 17 ml N,N-dimethylformamide diethylacetal. Reaction time is one hour at 100° C. After evaporation to dryness, the residue is crystallised in cyclohexane and pure yellow crystalline 3-N,N-dimethylaminomethylidene-6-fluoro-flavanone is obtained; m.p. 172°–173° C.

EXAMPLE 5

As in Example 4, but using 11 g 6-N,N-dimethylamino-flavanone, 110 ml dimethylformamide, and 35 ml N,N-dimethylformamide diethylacetal. Pure 6-N,N-dimethylamino-3-N,N-dimethylaminomethylidene-flavanone is obtained as yellow crystals after crystallisation in a mixture of hexane and ethyl acetate; m.p. 177°–178° C.

EXAMPLE 6

As in Example 4, but using 1 g 6-carboxy-flavanone, 10 ml dimethylformamide, 3 ml N,N-dimethylformamide diethylacetal. Pure 3-N,N-dimethylaminomethylidene-6-ethoxycarbonyl-flavanone is obtained as pale yellow crystals after crystallisation in diisopropylether; m.p. 128°-130° C.

EXAMPLE 7

As in Example 4, but using 1 g 7-hydroxy-flavanone, 10 ml dimethylformamide and 3 ml N,N-dimethylformamide dimethylacetal. Pure off-white crystalline 3-N,N-dimethylaminomethylidene-7-methoxy-flavanone is obtained after recrystallisation in a mixture of hexane and ethyl acetate; m.p. 179°-182° C.

EXAMPLE 8

As in Example 4, but using 5 g 7-hydroxy-flavanone, 50 ml dimethylformamide, and 18 ml N,N-dimethylformamide diethylacetal. Pure 3-N,N-dimethylaminomethylidene-7-ethoxy-flavanone is obtained as off-white crystals after crystallisation in a mixture of hexane and ethylacetate; m.p. 180°-185° C.

EXAMPLE 9

As in Example 4, but using 2 g 7-hydroxy-flavanone, 20 ml dimethylformamide and 9 ml N,N-dimethylformamide diisopropylacetal. Pure white crystalline 3-N,N-dimethylformamide diisopropylacetal. Pure white crystalline 3-N,N-dimethylaminomethylidene 7-isopropyloxy-flavanone is obtained after recrystallisation in a mixture of hexane and ethylacetate; m.p. 149°-151° C.

EXAMPLE 10

As in Example 4, but using 1 g 7-N,N-dimethylaminoflavanone, 10 ml dimethylformamide and 3 ml N,N-dimethylformamide diethylacetal. Pure 7-N,N-dimethylamino-3-N,N-dimethylaminomethylidene-flavanone is obtained as yellow crystals after recrystallisation in a mixture of toluene and hexane; m.p. 245°-255° C.

EXAMPLE 11

As in Example 4, but using 5 g 7-acetylamino-flavanone, 50 ml dimethylformamide and 15 ml N,N-dimethylformamide diethylacetal. Pure 7-acetylamino-3-N,N-dimethylaminomethylidene-flavanone is obtained as pale yellow crystals after crystallisation in a mixture of methylene chloride and ethylacetate; m.p. 240°-244° C.

EXAMPLE 12

As in Example 3 but using 9 g 7-fluoro-flavanone, 90 ml dimethylformamide and 32 ml N,N-dimethylformamide diethylacetal. Reaction time is one hour at 100° C. After evaporation to dryness, the residue is crystallised in cyclohexane and pure orange yellow crystalline 3-N,N-dimethylaminomethylidene-7-fluoro-flavanone is obtained; m.p. 142°-144° C.

EXAMPLE 13

As in Example 4, but using 1 g 4'-hydroxy-flavanone, 10 ml dimethylformamide and 3.5 ml N,N-dimethylformamide diethylacetal. After usual work up the residual solid is purified by column chromatography. The best fractions are recrystallised in a mixture of 2-butanone and diisopropylether and pure 3-N,N-dimethylaminomethylidene-4'-hydroxy-flavanone is obtained as pale yellow crystals; m.p. 200°-206° C.

EXAMPLE 14

As in Example 13 but after column chromatography a second set of fractions is obtained which gives a pale yellow resin after evaporation. This resin consists in pure 3-N,N-dimethylaminomethylidene-4'-ethoxy-flavanone. This resin is not recrystallised.

EXAMPLE 15

As in Example 1, but using 5 g 5,7-dimethoxy-flavanone, 50 ml dimethylformamide and 15 ml N,N-dimethylformamide diethylacetal. 5,7-dimethoxy-3-N,N-dimethylaminomethylidene-flavanone is obtained as off-white crystals after recrystallisation in a mixture of hexane and methylene chloride; m.p. 203°-208° C.

EXAMPLE 16

A suspension of 25 g 3-N,N-dimethylaminomethylidene-6-methyl-thioflavanone in 250 ml of a 4N hydrochloric acid solution is refluxed for five minutes. After cooling, the mixture is extracted with ether. The ethereal layer is washed with water and dried over magnesium sulfate. The residue obtained after evaporation of the ether is dissolved in 96% ethanol. Water is added dropwise with vigorous stirring to the filtered ethanol solution. Pure 3-hydroxymethylidene-6-methyl-thioflavanone crystallised as yellow crystals and is collected and dried; m.p. 85°-86° C.

EXAMPLE 17

A solution of 28.2 g 3-hydroxymethylidene-6-methyl-thioflavanone and 7.5 g glycine in 100 ml 96% ethanol, 100 ml water and 14 ml triethylamine is refluxed for two hours. After standing overnight at room temperature the precipitated crystals are filtered off. Ethanol is removed in vacuo and the remaining aqueous solution diluted with water to 800 ml. Acidification with a 4N hydrochloric acid solution led to precipitation of a product which is recrystallised from absolute ethanol. Pure 3-(N-carboxymethyl)aminomethylidene-6-methyl-thioflavanone is obtained as yellow crystals; m.p. 215°-222° C.

EXAMPLE 18

To a refluxing solution of 14 g 3-hydroxymethylidene-6-methyl-thioflavanone in 50 ml absolute ethanol is added a solution of 5.5 g o-aminophenol in 50 ml absolute ethanol. When an orange precipitate appeared the reaction mixture is cooled in ice and the crystals collected. The product is dissolved in boiling acetone, treated with charcoal and filtered. Slow addition of water to the stirred solution led to crystallisation of pure 3-(N-2-hydroxyphenyl)aminomethylidene-6-methyl-thioflavanone as orange crystals; m.p. 236°-243° C.

EXAMPLE 19

To a refluxing solution of 13 g sulfanilamide in 800 ml absolute ethanol is added 21 g 3-hydroxymethylidene-6-methyl-thioflavanone. After sixteen hours the reaction mixture is cooled and the crystals which separated are collected. After recrystallisation in a mixture of acetone and light petroleums, pure 3-(N-4-sulfamoylphenyl)aminomethylidene-6-methyl-thioflavanone is obtained as yellow crystals; m.p. 210°-213° C.

EXAMPLE 20

A 2N solution of methylmagnesium bromide in 75 ml ether is stirred under nitrogen at −10° C. 23 g 3-N,N- dimethylaminomethylidene-6-methyl-thioflavanone is added portionwise. After one hour, 150 ml tetrahydrofurane is added and the suspension stirred one hour longer. The mixture is allowed to stand overnight at room temperature and then poured into acidic water. Extraction with chloroform, washing with water, drying over magnesium sulfate and evaporation yielded a yellow oil. This oil is crystallised in a mixture of water and methanol and after drying pure 3-ethylidene-6-methyl-thioflavanone is obtained as pale yellow crystals; m.p. 63°–67° C.

EXAMPLE 21

A suspension of 16.8 g 3-N,N-dimethylaminomethylidene-flavanone in 200 ml of a 4N hydrochloric acid solution is refluxed for five minutes. Extraction with ether, washing with water and drying yielded a crude product which is refluxed in 150 ml isopropanol. 3-isopropyloxymethylidene-flavanone crystallised as yellow crystals; m.p. 142°–144° C.

EXAMPLE 22

A solution of 15 g 3-hydroxymethylidene-flavanone, 5.3 g glycine and 15 g sodium bicarbonate in 300 ml absolute ethanol is refluxed for 2 hours. After cooling with an ice bath, the precipitate is filtered, then dissolved in water and the solution acidified to pH 1. The precipitate is filtered, washed with water and dried. The solid is recrystallised in a mixture of hexane and ethylacetate. Pure 3-(N-carboxymethyl)aminomethylidene-flavanone is obtained as yellow crystals; m.p. 177°–181° C.

EXAMPLE 23

A suspension of 15 g 3-hydroxymethylidene-flavanone, 7.8 ml ethyl thioglycolate and 0.3 g para-toluenesulfonic acid in 150 ml absolute ethanol is stirred at room temperature for 20 hours. On cooling with an ice bath the product precipitates. After filtration and crystallisation in butanol pure 3-(S-ethoxycarbonylmethyl)-thiomethylidene-flavanone is obtained as yellow crystals; m.p. 96°–98° C.

EXAMPLE 24

A solution of 5.5 g sodium ethylate in 40 ml absolute ethanol is added to a suspension of 29.5 g 3-hydroxymethylidene-6-methyl-thioflavanone in 400 ml absolute ethanol. After stirring for one day at room temperature the suspension is poured into a mixture of water and chloroform containing acetic acid. The organic layer is separated and the aqueous layer is extracted with chloroform. The combined organic extracts are washed with water, dried over magnesium sulfate, filtered and evaporated. The residue is recrystallised from a mixture of light petroleum and chloroform. Pure 3-ethoxymethylidene-6-methyl-thioflavanone is obtained as yellow crystals; m.p. 140°–142° C.

EXAMPLE 25

A solution of 12.5 g glycine methylester hydrochloride and 14.1 g 3-hydroxymethylidene-6-methyl-thioflavanone in 250 ml 96% ethanol and 14 ml triethylamine is refluxed for 15 minutes. After cooling the reaction mixture is poured into a mixture of water and chloroform. The organic layer is separated and the aqueous layer extracted 3 times with chloroform. The combined organic extracts are dried over magnesium sulfate, filtered and evaporated. The residue is crystallised from a mixture of light petroleum and chloroform. Pure 3-(N-methoxycarbonylmethyl)aminomethylidene-6-methyl-thioflavanone is obtained as yellow crystals; m.p. 138°–140° C.

EXAMPLE 26

As in Example 25, but using glycine ethylester hydrochloride. Pure 3-(N-ethoxycarbonylmethyl)aminomethylidene-6-methylthioflavanone is obtained as yellow crystals; m.p. 131°–132° C.

EXAMPLE 27

A mixture of 17.6 g ethylbromoacetate, 28.3 g 3-hydroxymethylidene-6-methyl-thioflavanone and 13.8 g dry potassium carbonate in 130 ml dry acetone is refluxed for one hour and a half. After cooling the mixture is poured into a mixture of chloroform and water. The organic layer is separated and the aqueous layer extracted with chloroform. The combined organic extracts are dried over magnesium sulfate, filtered and evaporated. The residue is crystallised from a mixture of light petroleum and chloroform. Pure 3-(0-ethoxycarbonylmethyl)oxymethylidene-6-methyl-thioflavanone is obtained as yellow crystals; m.p. 110°–112° C.

EXAMPLE 28

A mixture of 6.5 g 3-hydroxymethylidene-flavanone, 3.6 g dry potassium carbonate and 3.4 ml ethylbromoacetate in 65 ml dry acetone is stirred 3 hours at room temperature. The precipitate which forms is filtered. The filtrate is evaporated under vacuo and the residue dissolved in methylene chloride. This solution is washed with water, dried over magnesium sulfate and evaporated. The residual solid is recrystallized in ethanol. Pure 3-(0-ethoxycarbonylmethyl)oxymethylidene-flavanone is obtained as white crystals; m.p. 129°–131° C.

EXAMPLE 29

A solution containing 6 g 3-N,N-dimethylaminomethylidenethioflavanone in 60 ml 4N-hydrochloric acid aqueous solution is refluxed for five minutes then cooled on an ice bath. The oil formed is decanted and dissolved in methylene chloride. The organic solution is washed with water, dried over magnesium sulfate and evaporated. Pure 3-hydroxymethylidene-thioflavanone is obtained as a yellow oil.

EXAMPLE 30

A solution of 1.41 g 3-hydroxymethylidene-6-methyl-thioflavanone and 1.53 g sarcosine ethyl ester hydrochloride in 10 ml 96% ethanol containing 1.5 ml triethylamine is refluxed for 30 minutes. The cooled reaction mixture is poured into a mixture of water and chloroform. After separation of the layers, the aqueous layer is extracted twice with chloroform. The combined chloroform extracts are washed with water and dried over magnesium sulfate. Evaporation gives a yellow oil which is purified by column chromatography on silicagel using a mixture of methylene chloride and methanol. The best fractions are crystallized from a mixture of light petroleum, b.p. 60°–80° C. and chloroform. Pure 3-(N-methyl-N-ethoxycarbonylmethyl)aminomethylidene-6-methyl-thioflavanone is obtained as yellow crystals; m.p. 120°–122° C.

EXAMPLE 31

As in example 18 but starting from 5 g 3-hydroxymethylideneflavanone and 2.16 g o-aminophenol. Pure 3-(N-2-hydroxyphenyl)aminomethylidene-flavanone is obtained as yellow crystals; m.p. 226°–228° C.

EXAMPLE 32

A solution containing 23.8 g methylmagnesium iodide in 70 ml ether is stirred under nitrogen at −10° C. A solution of 20 g 3-N,N-dimethylaminomethylideneflavanone in 140 ml tetrahydrofurane is added slowly. After one hour, the suspension is poured into acidic water. Extraction with chloroform, washing with water, drying over magnesium sulfate and evaporation yielded a yellow oil. This oil is purified by preparative HPLC. Pure 3-ethylidene-flavanone is obtained as pale yellow crystals; m.p. 47°–49° C.

EXAMPLE 33

A solution containing 10 g 3-hydroxymethylideneflavanone and 3.6 ml pyrrolidine in 100 ml absolute ethanol is refluxed for 15 minutes, then cooled on an ice bath. The precipitate which forms is filtered and recrystallized in a mixture of hexane and ethyl acetate. Pure 3-N-pyrrolidinomethylidene-flavanone is obtained as pale yellow crystals; m.p. 193°–194° C.

EXAMPLE 34

A solution containing 17 g 3-hydroxymethylideneflavanone and 6.4 ml isopropylamine in 170 ml absolute ethanol is refluxed for 10 minutes then cooled on an ice bath. After evaporation of the solution the resulting oil is dissolved in methylene chloride. This solution is washed with acidic water then with water to pH 7 dried over magnesium sulfate and evaporated. The resulting solid is crystallized in cyclohexane. Pure 3-N-isopropylaminomethylideneflavanone is obtained as yellow crystals; m.p. 100°–105° C.

EXAMPLE 35

A solution containing 1 g 3-hydroxymethylideneflavanone and 0.4 ml diethanolamine in 10 ml absolute ethanol is refluxed for 10 minutes then cooled on an ice bath. After evaporation, the resulting oil is crystallized in methylene chloride. Pure 3-N,N-di(2-hydroxyethyl)aminomethylidene-flavanone is obtained as pale yellow crystals; m.p. 153°–157° C.

EXAMPLE 36

A solution containing 1 g 3-hydroxymethylideneflavanone and 0.3 g imidazole in 10 ml absolute ethanol is refluxed for 10 minutes then cooled on an ice bath. After evaporation the oil is dissolved in methylene chloride and purified by acidic extraction. The resulting oil is crystallized in a mixture of hexane and ethyl acetate. Pure 3-(1-imidazolyl)methylidene-flavanone is obtained as white crystals; m.p. 129°–131° C.

EXAMPLE 37

A mixture containing 10.1 g 3-hydroxymethylideneflavanone, 1.4 g tetrabutylammoniumhydrogensulfate, 10.3 ml ethylmethylamine and 100 ml toluene is stirred 2 days at 50° C. After cooling to room temperature, the precipitate is filtered off, and the organic phase is washed with water, dried and evaporated. The resulting solid is crystallized in a mixture of hexane and toluene. Pure 3-N-ethyl-N-methylaminomethylidene-flavanone is obtained as pale yellow crystals; m.p. 157°–158° C.

EXAMPLE 38

A solution containing 5.05 g of 3-hydroxymethylidene-flavanone and 6.2 ml dimethylamine in 50 ml absolute ethanol is refluxed for 90 minutes then cooled on an ice bath. After evaporation the oil is crystallized in diisopropylether. Pure 3-N,N-diethylaminomethylideneflavanone is obtained as pale yellow crystals; m.p. 133°–135° C.

EXAMPLE 39

As in example 37 but using 10.3 ml of 40% aqueous solution of methylamine. After work up the resulting oil is purified by preparative HPLC and the best fractions recrystallized in a mixture of cyclohexane and diisopropylether. Pure 3-N-methylaminomethylidene-flavanone is obtained as pale yellow crystals; m.p. 100°–104° C.

EXAMPLE 40

A solution containing 30.3 g 3-hydroxymethylideneflavanone, 18.5 g ammonium acetate, and 6 ml glacial acetic acid in 300 ml toluene is refluxed for one hour. After cooling the solution is neutralized with a saturated sodium bicarbonate aqueous solution. The precipitate is filtered off, then dissolved in methylene chloride, washed with water, dried and evaporated. Pure 3-aminomethylidene-flavanone is obtained as pale yellow crystals; m.p. 149°–152° C.

EXAMPLE 41

A solution containing 12.5 g 3-aminomethylideneflavanone, 7.85 g acetyl chloride in 100 ml pyridine is stirred at room temperature for one hour. After evaporation the resulting solid is dissolved in methylene chloride, washed with 1N hydrochloric acid solution, then with water, dried and evaporated. The curde product is recrystallized in methanol. Pure 3-N-acetylaminomethylidene-flavanone is obtained as yellow crystals; m.p. 150° C.

EXAMPLE 42

A cooled solution of 8.04 g 3-N,N-dimethylaminomethylidene-6-methyl-thioflavanone and 7.5 g meta-chloroperbenzoic acid in 80 ml methylene chloride is stirred at 0° C. for 30 minutes. After filtration the organic phase is washed with 5% sodium bicarbonate aqueous solution, then with water, dried over magnesium sulfate and evaporated. The crude product is crystallized in a mixture of diisopropyl ether and 2-butanone. Pure 3-N,N-dimethylaminomethylidene-6-methyl-thioflavanone-1-oxide is obtained as yellow crystals; m.p. 201°–203° C.

EXAMPLE 43

A solid mixture of 9 g flavanone, 7.2 g 3-acetylaminobenzaldehyde and 5 drops piperidine is heated at 150°–160° C. for 3 hours. After allowing to cool, the crude brown glass is dissolved in chloroform and eluted from silicagel with chloroform. The pale yellow oil, obtained on evaporation of the solvent is crystallized from hexane and ethyl acetate to give 3(3-acetylaminobenzylidene)-flavanone as a cream coloured solid; m.p. 172°–173° C.

EXAMPLE 44

A solid mixture of 10 g 6-methyl-thioflavanone, 13 g 4-acetylaminobenzaldehyde and 8 drops piperidine is heated at 150°–160° C. for 3 hours. After allowing to cool, the crude brown glass is crystallized from ethanol. Pure 3-(4-acetylaminobenzylidene)-6-methyl-thioflavanone is obtained as a yellow solid; m.p. 197°–198° C.

EXAMPLE 45

A solution of 2.7 g 3-chloromethylidene-flavanone and 0.95 g piperazine in 50 ml tetrahydrofuran is stirred at room temperature for 4 hours. After solvent evaporation, the crude solid is recrystallized in toluene. Pure 3,3'-(1,4-N,N'-piperazino)methylidene-diflavanone, i.e. 3-[4-(2",3"-dihydro-2"-phenyl-4"H-1"-benzopyran-4-on-3"-ylidenemethyl)piperazin-1-yl]-methylidene-flavanone, is obtained as white crystals; m.p. 205°–210° C.

EXAMPLE 46

A mixture of 5 g 3-hydroxymethylidene-flavanone and 9 g 4-carboxybenzylamine in 50 ml dry ethanol is stirred under nitrogen and reflux for 30 minutes. After filtration and washing of the solid with warm ethanol, the filtrate is cooled with an ice bath. A yellow precipitate forms which is filtered, dried and recrystallized in toluene. Pure yellow crystalline 3-[N-(4-carboxybenzyl)amino]methylidene-flavanone is obtained; m.p. 195°–200° C.

EXAMPLE 47

A cooled solution of 0.28 g 3-ethylidene-6-methyl-thioflavanone and 0.2 g meta-chloroperbenzoic acid in 3 ml methylene chloride is stirred at 0° C. for 5 minutes. After filtration the organic phase is washed with saturated sodium bicarbonate aqueous solution, then with water, dried over magnesium sulfate and evaporated. The crude solid is crystallized in cyclohexane. Pure 3-ethylidene-6-methyl-thioflavanone-1-oxide is obtained as yellow crystals; m.p. 151°–160° C.

EXAMPLE 48

As in example 47, but starting with 0.28 g 3-hydroxymethylidene-6-methyl-thioflavanone. After work-up the crude solid is purified by column chromatography using hexane and acetone as eluting system. The best fractions are collected. Pure 3-hydroxymethylidene-6-methyl-thioflavanone-1-oxide is obtained as a yellow solid; m.p. 101°–110° C.

EXAMPLE 49

As in example 47, but starting with 0.4 g 3-(4-acetylaminobenzylidene)-6-methyl-thioflavanone. After work-up the crude solid is crystallized in methanol. Pure 3-(4-acetylaminobenzylidene)-6-methyl-thioflavanone-1-oxide is obtained as yellow crystals; m.p. 259°–269° C.

EXAMPLE 50

A solution of 1 g 3-ethylidene-6-methyl-thioflavanone, 100 mg selenium dioxide, 3.65 ml 30% hydrogen peroxide in 10 ml dioxane is warmed at 70° C. for 5 hours. Water is added and extraction with methylene chloride is followed by drying over magnesium sulfate and evaporation. The resulting white solid is purified by column chromatography over silicagel using methylene chloride as eluant. The best fractions are are mixed and recrystallised in a mixture of hexane and toluene. Pure 3-ethylidene-6-methyl-thioflavanone-1,1-dioxide is obtained as white crystals; m.p. 163°–174° C.

I claim:

1. A compound of the formula I

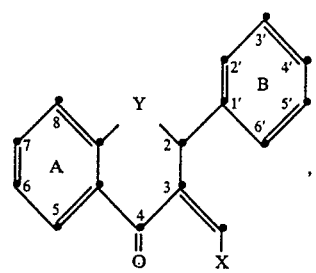

wherein X is amino; lower alkylamino the alkyl portion of which is unsubstituted or substituted by carboxy, lower alkoxycarbonyl, hydroxy or phenyl that in turn is unsubstituted or substituted by carboxy or lower alkoxycarbonyl; $N$-$(C_1$-$C_7)$alkyl-$N$-$(C_2$-$C_7)$alkylamino the alkyl portions of which are unsubstituted or substituted by carboxy, lower alkoxycarbonyl, or hydroxy; lower alkyleneamino having 5 to 7 ring members; phenylamino the phenyl portion of which is unsubstituted or substituted by hydroxy, lower alkoxy, sulfo, sulfamoyl, N-lower alkylsulfamoyl, or N,N-di-lower alkylsulfamoyl; lower alkanoylamino; lower alkoxy which is unsubstituted or substituted by carboxy or lower alkoxycarbonyl; lower alkylthio which is unsubstituted or substituted by carboxy or lower alkoxycarbonyl;

Y is oxygen, sulfur, sulfinyl or sulfonyl; and the rings A and B are independently unsubstituted or mono- or disubstituted by hydroxy, halogen, lower alkyl, lower alkoxy, lower alkylamino, di-lower alkylamino, lower alkanoylamino, carboxy or lower alkoxycarbonyl;

or a pharmaceutically acceptable salt thereof.

2. A compound of the formula I

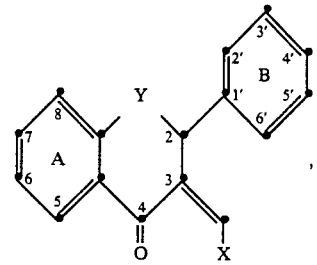

wherein X is dimethylamino, or hydroxy; Y is oxygen; and A and B are aromtic rings of which at least one is mono- or disubstituted by hydroxy, halogen, lower alkyl, lower alkoxy, lower alkylamino, di-lower alkylamino, lower alkanoylamino, carboxy or lower alkoxycarbonyl; or a pharmaceutically acceptable salt thereof.

3. A compound of the formula I

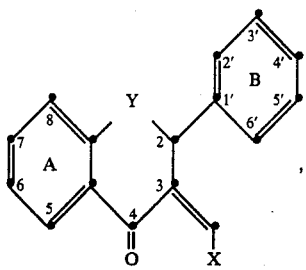

wherein X is dimethylamino; Y is sulfur, sulfinyl or sulfonyl; and the rings A and B are independently unsubstituted or mono- or disubstituted by hydroxy, halogen, lower alkyl, lower alkoxy, lower alkylamino, di-lower alkylamino, lower alkanoylamino, carboxy or lower alkoxycarbonyl; or a pharmaceutically acceptable salt thereof.

4. A compound of the formula I

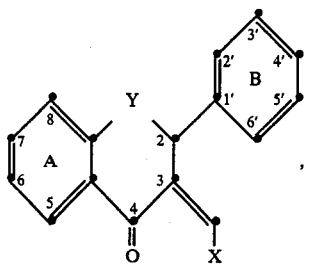

wherein Y is sulfur and X is phenyl substituted by lower alkanoylamino; and
the rings A and B are independently unsubstituted or substituted by 1 or 2 substituents selected from the group consisting of hydroxy; lower alkoxy; lower alkanoyloxy; di-lower alkylamino; lower alkanoylamino; lower alkyl; halogen; carboxy; or lower alkoxycarbonyl; or a pharmaceutically acceptable salt thereof.

5. A compound of the formula I

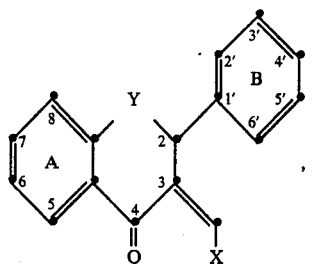

wherein X is 1H-imidazol-1-yl; Y is oxygen or sulfonyl; and the rings A and B are independently unsubstituted or substituted by 1, or 2 substituents of the group consisting of hydroxy, lower alkoxy, lower alkylamino, di-lower alkylamino, lower alkanoylamino, lower alkyl, halogen, carboxy, or lower alkoxycarbonyl; or a pharmaceutically acceptable salt thereof.

6. 3-(N-Methyl-N-ethoxycarbonylmethyl)aminomethylidene-6-methyl thioflavanone, or a pharmaceutically acceptable salt thereof.

7. 3-[4-(2",3"-Dihydro-2"-phenyl-4"H-1"-benzopyran-4"-on-3"-ylidenemethyl)-piperazin-1-yl]-methylidene-flavanone, or a pharmaceutically acceptable salt thereof.

8. 3-Hydroxymethylidene-6-methyl-thioflavanone-1-oxide.

9. 3-[4-(N-Acetylaminobenzylidene)]-6-methyl-thioflavanone-1-oxide, or a pharmaceutically acceptable salt thereof.

10. 3-[4-(N-Acetylaminobenzylidene)]-6-methyl-thioflavanone, or a pharmaceutically acceptable salt thereof, according to claim 4.

11. 3-(1-Imidazolyl)methylidene-flavanone, or a pharmaceutically acceptable salt thereof, according to claim 5.

12. 3-(N-Acetylaminomethylidene)-flavanone, or a pharmaceutically acceptable salt thereof, according to claim 1.

13. An antiedema composition comprising a therapeutically effective amount of a compound of claim 1 or a pharmaceutically acceptable salt thereof and a pharmaceutically acceptable carrier.

14. An antiedema composition comprising a therapeutically effective amount of a compound of claim 2 or a pharmaceutically acceptable salt thereof and a pharmaceutically acceptable carrier.

15. An antiedema composition comprising a therapeutically effective amount of a compound of claim 3 or a pharmaceutically acceptable salt thereof and a pharmaceutically acceptable carrier.

16. An antiedema composition comprising a therapeutically effective amount of a compound of claim 4 or a pharmaceutically acceptable salt thereof and a pharmaceutically acceptable carrier.

17. An antiedema composition comprising a therapeutically effective amount of a compound of claim 5 or a pharmaceutically acceptable salt thereof and a pharmaceutically acceptable carrier.

18. A method of treating edema in a mammal in need thereof comprising administering to said mammal an anti edema effective amount of a compound of claim 1 or a pharmaceutically acceptable salt thereof.

19. A method of treating edema in a mammal in need thereof comprising administering to said mammal an anti edema effective amount of a compound of claim 2 or a pharmaceutically acceptable salt thereof.

20. A method of treating edema in a mammal in need thereof comprising administering to said mammal an anti edema effective amount of a compound of claim 3 or a pharmaceutically acceptable salt thereof.

21. A method of treating edema in a mammal in need thereof comprising administering to said mammal an anti edema effective amount of a compound of claim 4 or a pharmaceutically acceptable salt thereof.

22. A method of treating edema in a mammal in need thereof comprising administering to said mammal an anti edema effective amount of a compound of claim 5 or a pharmaceutically acceptable salt thereof.

23. 3-isopropyloxymethylidene-flavanone according to claim 1.

24. 3-N-isopropylaminomethylidene-flavanone as a pharmaceutically acceptable salt thereof according to claim 1.

25. 3-N,N-diethylaminomethylidene-flavanone or a pharmaceutically acceptable salt thereof according to claim 1.

26. An antiedema composition comprising a therapeutically effective amount of a compound selected from a compound of the formula

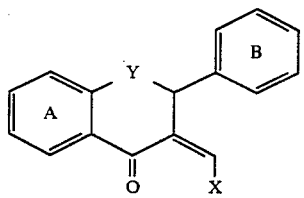

wherein
(a) X is lower alkyl; Y is oxygen, sulfur, sulfinyl, or sulfonyl; and rings A and B are independently unsubstituted or mono or di-substituted by hydroxy, halogen, lower alkyl, lower alkoxy, lower alkylamino, dilower alkylamino, lower alkanoylamino, carboxy, or lower alkoxycarbonyl; and
(b) X is phenyl substituted by lower alkanoylamino in the 2-or 3-position; Y is oxygen; and
the rings A and B are independently unsubstituted or substituted by one or 2 substituents selected from hydroxy, lower alkoxy, lower alkylamino, dilower alkylamino, lower alkanoylamino, lower alkyl, halogen, carboxy, and lower alkoxycarbonyl; or a pharmaceutically acceptable salt thereof, together with a pharmaceutically acceptable carrier.

27. A method of treating edema in a mammal in need thereof comprising administering to said mammal an antiedema effective amount of a compound of the formula

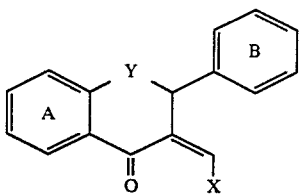

wherein
(a) X is lower alkyl; Y is oxygen, sulfur, sulfinyl, or sulfonyl; and rings A and B are independently unsubstituted or mono or di-substituted by hydroxy, halogen, lower alkyl, lower alkoxy, lower alkylamino, dilower alkylamino, lower alkanoylamino, carboxy, or lower alkoxycarbonyl; and
(b) X is phenyl substituted by lower alkanoylamino in the 2-or 3-position; Y is oxygen; and the rings A and B are independently unsubstituted or substituted by one or 2 substituents selected from hydroxy, lower alkoxy, lower alkylamino, dilower alkylamino, lower alkanoylamino, lower alkyl, halogen, carboxy, and lower alkoxycarbonyl; or a pharmaceutically acceptable salt thereof.

* * * * *